US012414920B2

(12) United States Patent
Fischer et al.

(10) Patent No.: US 12,414,920 B2
(45) Date of Patent: *Sep. 16, 2025

(54) SPRAY-DRIED BLOOD PRODUCTS AND METHODS OF MAKING SAME

(71) Applicant: Velico Medical, Inc., Beverly, MA (US)

(72) Inventors: Thomas H. Fischer, Durham, NC (US); Joseph A DaCorta, Durham, NC (US); Michael Lawrence Galiger, Durham, NC (US)

(73) Assignee: Velico Medical Inc., Beverly, MA (US)

( * ) Notice: Subject to any disclaimer, the term of this patent is extended or adjusted under 35 U.S.C. 154(b) by 85 days.

This patent is subject to a terminal disclaimer.

(21) Appl. No.: 17/566,226

(22) Filed: Dec. 30, 2021

(65) Prior Publication Data

US 2022/0117897 A1    Apr. 21, 2022

Related U.S. Application Data

(60) Division of application No. 15/872,727, filed on Jan. 16, 2018, now Pat. No. 11,213,488, which is a continuation of application No. 13/262,931, filed as application No. PCT/US2010/030031 on Apr. 6, 2010, now Pat. No. 9,867,782.

(60) Provisional application No. 61/212,321, filed on Apr. 9, 2009.

(51) Int. Cl.
*A61K 9/16* (2006.01)
*A61F 13/00* (2024.01)
*A61K 9/00* (2006.01)
*A61K 35/16* (2015.01)
*A61K 35/19* (2015.01)
*A61L 15/40* (2006.01)
*A61L 26/00* (2006.01)

(52) U.S. Cl.
CPC ...... *A61K 9/1688* (2013.01); *A61F 13/00063* (2013.01); *A61K 9/0026* (2013.01); *A61K 35/16* (2013.01); *A61K 35/19* (2013.01); *A61L 15/40* (2013.01); *A61L 26/0047* (2013.01); *A61L 26/0057* (2013.01); *A61L 26/0076* (2013.01); *A61F 2013/00306* (2013.01); *A61F 2013/00472* (2013.01); *A61F 2013/00927* (2013.01)

(58) Field of Classification Search
None
See application file for complete search history.

(56) References Cited

U.S. PATENT DOCUMENTS

| | | |
|---|---|---|
| 2,362,025 A | 1/1943 | Price |
| 2,411,152 A | 11/1946 | Folsom |
| 2,528,476 A | 10/1950 | Roos et al. |
| 2,575,175 A | 11/1951 | Kronisch |
| 3,228,838 A | 1/1966 | Rinfret et al. |
| 3,230,689 A | 1/1966 | Hussmann |
| 3,449,124 A | 6/1969 | Lipner |
| 3,507,278 A | 4/1970 | Werding |
| 3,644,128 A | 2/1972 | Lipner |
| 3,654,705 A | 4/1972 | Smith et al. |
| 3,693,886 A | 9/1972 | Conrad |
| 3,735,792 A | 5/1973 | Asizawa et al. |
| 3,945,574 A | 3/1976 | Polnauer |
| 4,187,617 A | 2/1980 | Becker et al. |
| 4,251,510 A | 2/1981 | Tankersley |
| 4,347,259 A | 8/1982 | Suzuki et al. |
| 4,358,901 A | 11/1982 | Takabatake et al. |
| 4,376,010 A | 3/1983 | Gauvin |
| 4,378,346 A | 3/1983 | Tankersley |
| 4,380,491 A | 4/1983 | Joy |
| 4,422,900 A | 12/1983 | Bordelon |
| 4,597,868 A | 7/1986 | Watanabe |
| 4,600,613 A | 7/1986 | Yoshida |
| 4,645,482 A | 2/1987 | Yoshida |

(Continued)

FOREIGN PATENT DOCUMENTS

| | | |
|---|---|---|
| AU | 2010234607 | 10/2010 |
| CA | 1182411 | 2/1985 |

(Continued)

OTHER PUBLICATIONS

Polo, J. et al., Efficacy of spray-drying to reduce infectivity of pseudorabie and porcine reproductive and respiratory syndrome (PRRS) viruses and seroconversion in p. fed diets containing spray-dried animal plasma, Journal of Animal Science, Aug. 2005, vol. 83, No. 8, pp. 1933-1938.

Hawksworth, J.S. et al., Evaluation of lyophilized platelets as an infusible hemostatic agent in experimental non-compressible hemorrhage in swine, Journal of Thrombosis and Haemostasis, Oct. 2009, vol. 7, No. 10, pp. 1663-1671.

Shuja, Fahad et al., Development and Testing of Low-Volume Hyperoncotic, Hyperosmotic Spray-Dried Plasma for the Treatment of Trauma-Associated Coagulopathy, Journal of Trauma Injury Infection and Critical Care, Mar. 2011, vol. 70, No. 3. pp. 664-671.

(Continued)

*Primary Examiner* — Teresa E Knight
(74) *Attorney, Agent, or Firm* — Antoinette G. Giugliano PC; Antoinette G Giugliano

(57) ABSTRACT

The present invention is directed to a method of preparing dehydrated blood products, comprising the steps of: (a) providing a hydrated blood product; (b) spray-drying the hydrated blood product to produce a dehydrated blood product, as well as dehydrated blood products made by the method. The present invention is directed to a method of treating a patient suffering from a blood-related disorder, comprising the steps of: (a) rehydrating a therapeutic amount of the dehydrated blood products to produce a rehydrated therapeutic composition; and (b) administering the rehydrated therapeutic composition to the patient. The present invention is directed to a bandage or surgical aid comprising the dehydrated blood products described above.

12 Claims, 5 Drawing Sheets

(56) References Cited

U.S. PATENT DOCUMENTS

| | | |
|---|---|---|
| 4,705,612 A | 11/1987 | Shimomura et al. |
| 4,725,355 A | 2/1988 | Yamamoto et al. |
| 4,735,832 A | 4/1988 | Ichikawa et al. |
| 4,743,375 A | 5/1988 | Seita et al. |
| 4,774,019 A | 9/1988 | Watanabe et al. |
| 4,787,154 A | 11/1988 | Titus |
| 4,845,132 A | 7/1989 | Masuoka et al. |
| 4,861,632 A | 8/1989 | Caggiano |
| 4,966,699 A | 10/1990 | Sasaki et al. |
| 5,096,537 A | 3/1992 | Bergquist et al. |
| 5,139,529 A | 8/1992 | Seita et al. |
| 5,145,706 A | 9/1992 | Jagi et al. |
| 5,167,763 A | 12/1992 | Sakamoto |
| 5,181,415 A | 1/1993 | Esvan et al. |
| 5,227,017 A | 7/1993 | Tanaka |
| 5,244,578 A | 9/1993 | Ohnishi et al. |
| 5,252,221 A | 10/1993 | van Dommelen et al. |
| 5,254,248 A | 10/1993 | Nakamura |
| 5,257,983 A | 11/1993 | Garyantes et al. |
| 5,267,646 A | 12/1993 | Inoue et al. |
| 5,279,738 A | 1/1994 | Seita et al. |
| 5,309,649 A | 5/1994 | Bergmann et al. |
| 5,372,811 A | 12/1994 | Yoder |
| 5,447,077 A | 9/1995 | Lautenschlager |
| 5,499,768 A | 3/1996 | Tanaka |
| 5,522,156 A | 6/1996 | Ware |
| 5,523,004 A | 6/1996 | Tanokura et al. |
| 5,529,821 A | 6/1996 | Ishikawa et al. |
| 5,547,576 A | 8/1996 | Onishi et al. |
| 5,562,919 A | 10/1996 | Doty et al. |
| 5,567,238 A | 10/1996 | Long, Jr. |
| 5,575,999 A | 11/1996 | Yoder |
| 5,581,903 A | 12/1996 | Botich |
| 5,582,794 A | 12/1996 | Hagiwara et al. |
| 5,624,530 A | 4/1997 | Sadykhov |
| 5,647,142 A | 7/1997 | Andersen et al. |
| 5,657,555 A | 8/1997 | Milojevic |
| 5,680,712 A | 10/1997 | Kiyokawa |
| 5,610,170 A | 11/1997 | Inoue et al. |
| 5,727,333 A | 3/1998 | Folan |
| 5,838,515 A | 11/1998 | Mortazavi et al. |
| 5,924,216 A | 7/1999 | Takahashi |
| 5,993,804 A | 11/1999 | Read et al. |
| 6,004,576 A | 12/1999 | Weaver et al. |
| 6,005,857 A | 12/1999 | Honkasalo et al. |
| 6,060,323 A | 5/2000 | Jina |
| D430,939 S | 9/2000 | Zukor et al. |
| 6,148,536 A | 11/2000 | Lijima |
| 6,197,289 B1 | 3/2001 | Wirt et al. |
| 6,223,455 B1 | 5/2001 | Chickering, III |
| 6,284,282 B1 | 9/2001 | Maa et al. |
| 6,299,906 B1 | 10/2001 | Bausch et al. |
| 6,308,434 B1 | 10/2001 | Chickering et al. |
| 6,308,826 B1 | 10/2001 | Merrell |
| 6,345,452 B1 | 2/2002 | Feuilloley et al. |
| 6,463,675 B1 | 10/2002 | Hansen et al. |
| 6,523,276 B1 | 2/2003 | Meldrum |
| 6,582,654 B1 | 2/2003 | Kral et al. |
| 6,526,774 B1 | 3/2003 | Lu et al. |
| 6,560,897 B2 | 5/2003 | Chickering et al. |
| 6,569,447 B2 | 5/2003 | Kisic et al. |
| 6,723,497 B2 | 4/2004 | Wolkers et al. |
| 6,762,336 B1 * | 7/2004 | MacPhee ............ A61L 15/26 602/42 |
| 6,893,412 B2 | 5/2005 | Saito et al. |
| 7,005,857 B2 | 2/2006 | Stiene et al. |
| 7,007,405 B2 | 3/2006 | Hajek et al. |
| 7,007,406 B2 | 3/2006 | Wang et al. |
| 7,074,582 B2 | 7/2006 | Fischer et al. |
| 7,089,681 B2 | 8/2006 | Herbert et al. |
| 7,094,378 B1 | 8/2006 | Goodrich, Jr. et al. |
| 7,297,716 B2 | 11/2007 | Shanbrom |
| 7,361,306 B2 | 4/2008 | Bole |
| 7,399,637 B2 | 7/2008 | Wright et al. |
| 7,419,682 B2 | 9/2008 | Campbell et al. |
| 7,527,805 B2 | 5/2009 | Crenshaw et al. |
| 7,648,699 B2 | 1/2010 | Goodrich et al. |
| 7,931,919 B2 | 4/2011 | Bakaltcheva et al. |
| 7,993,310 B2 | 8/2011 | Rosiello |
| 8,322,046 B2 | 12/2012 | Wang et al. |
| 8,398,732 B2 | 3/2013 | Turok et al. |
| 8,407,912 B2 | 4/2013 | Hubbard et al. |
| 8,434,242 B2 | 5/2013 | Hubbard et al. |
| 8,449,520 B2 | 5/2013 | Pepper et al. |
| 8,469,202 B2 | 6/2013 | Rosiello |
| 8,518,452 B2 | 8/2013 | Bjornstrup et al. |
| 8,533,971 B2 | 9/2013 | Hubbard et al. |
| 8,533,972 B2 | 9/2013 | Hubbard et al. |
| 8,595,950 B2 | 12/2013 | Hubbard et al. |
| 8,601,712 B2 | 12/2013 | Hubbard et al. |
| 8,968,879 B2 | 3/2015 | Inaba et al. |
| 9,440,011 B2 | 9/2016 | Van Waeg et al. |
| 9,453,676 B2 | 9/2016 | Robinson |
| 9,545,379 B2 | 1/2017 | Liu et al. |
| 9,551,527 B2 | 1/2017 | Beetz |
| 9,561,184 B2 | 2/2017 | Khan et al. |
| 9,561,893 B2 | 2/2017 | Root et al. |
| 9,863,699 B2 | 1/2018 | Corbin, III et al. |
| 9,867,782 B2 | 1/2018 | Fischer et al. |
| 9,915,473 B2 | 3/2018 | Ilan |
| 10,022,478 B2 | 7/2018 | Anzai et al. |
| 10,251,911 B2 | 4/2019 | DaCorta et al. |
| 10,279,359 B2 | 5/2019 | Ackerman |
| 10,376,614 B2 | 8/2019 | Kohama et al. |
| 10,376,809 B2 | 8/2019 | Nielsen |
| 10,377,520 B2 | 8/2019 | Root et al. |
| 10,539,367 B2 | 1/2020 | Corbin, III et al. |
| 10,793,327 B2 | 10/2020 | Weimer et al. |
| 10,806,665 B2 | 10/2020 | Murto |
| 10,843,100 B2 | 11/2020 | Khan et al. |
| 10,960,023 B2 | 3/2021 | DaCorta et al. |
| 10,969,171 B2 | 4/2021 | Corbin, III et al. |
| 11,052,045 B2 | 7/2021 | Liu et al. |
| 11,213,488 B2 | 1/2022 | Fischer et al. |
| 11,841,189 B1 | 12/2023 | Andrews |
| 11,913,722 B1 | 2/2024 | Andrews |
| 11,913,723 B1 | 2/2024 | Andrews |
| 11,975,274 B2 | 5/2024 | Liu |
| 11,998,861 B2 | 6/2024 | Andrews |
| 2002/0056206 A1 | 5/2002 | Pace |
| 2002/0122803 A1 | 9/2002 | Kisic et al. |
| 2002/0182195 A1 | 12/2002 | Marguerre et al. |
| 2003/0037459 A1 | 2/2003 | Checkering, III et al. |
| 2003/0099633 A1 | 5/2003 | Campbell et al. |
| 2003/0103962 A1 | 6/2003 | Campbell et al. |
| 2003/0143518 A1 | 7/2003 | Luck et al. |
| 2003/0163931 A1 | 9/2003 | Beyerinck |
| 2003/0180283 A1 | 9/2003 | Batycky et al. |
| 2003/0186004 A1 | 10/2003 | Koslow |
| 2003/0190314 A1 | 10/2003 | Campbell et al. |
| 2003/0209245 A1 | 11/2003 | Poole et al. |
| 2004/0058309 A1 | 3/2004 | Washizu |
| 2004/0086420 A1 | 5/2004 | MacPhee |
| 2004/0110871 A1 | 6/2004 | Perrut et al. |
| 2004/0146565 A1 | 7/2004 | Stronbehn et al. |
| 2004/0175296 A1 | 9/2004 | Opalsky et al. |
| 2004/0202660 A1 | 10/2004 | Campbell et al. |
| 2004/0247628 A1 | 12/2004 | Lintz et al. |
| 2005/0142208 A1 | 6/2005 | Yoo |
| 2005/0170068 A1 | 8/2005 | Roodink et al. |
| 2005/0186183 A1 | 8/2005 | DeAngelo et al. |
| 2005/0271626 A1 | 12/2005 | Campbell et al. |
| 2006/0045907 A1 | 3/2006 | Campbell et al. |
| 2006/0088642 A1 | 4/2006 | Boersen et al. |
| 2006/0130768 A1 | 6/2006 | Crenshaw et al. |
| 2006/0216687 A1 | 9/2006 | Alves-Filho et al. |
| 2006/0222980 A1 | 10/2006 | Makino et al. |
| 2007/0014806 A1 | 1/2007 | Marguerre et al. |
| 2007/0084244 A1 | 4/2007 | Rosenflanz et al. |
| 2007/0166389 A1 | 7/2007 | Bakaltcheva |
| 2008/0058469 A1 | 3/2008 | Abe et al. |
| 2008/0060213 A1 | 3/2008 | Gehrmann et al. |
| 2008/0119818 A1 | 5/2008 | Bakaltcheva et al. |
| 2008/0138340 A1 | 6/2008 | Campbell et al. |

(56) References Cited

U.S. PATENT DOCUMENTS

| | | |
|---|---|---|
| 2008/0145444 A1 | 6/2008 | Merchant et al. |
| 2008/0145834 A1 | 6/2008 | Ho |
| 2008/0213263 A1 | 9/2008 | Campbell et al. |
| 2008/0234653 A1 | 9/2008 | McCarthy et al. |
| 2008/0317640 A1 | 12/2008 | Mayer |
| 2009/0092678 A1 | 4/2009 | Marguerre et al. |
| 2009/0155410 A1 | 4/2009 | Crenshaw et al. |
| 2009/0113753 A1 | 5/2009 | Pepper et al. |
| 2009/0145783 A1 | 6/2009 | Forker |
| 2009/0223080 A1 | 9/2009 | McCarthy |
| 2010/0011610 A1 | 1/2010 | Bittorf |
| 2010/0108183 A1 | 5/2010 | Rosiello |
| 2010/0215667 A1 | 8/2010 | Campbell et al. |
| 2010/0233671 A1 | 9/2010 | Bakaltcheva |
| 2010/0273141 A1 | 10/2010 | Bakaltcheva |
| 2011/0142885 A1 | 6/2011 | Haley et al. |
| 2011/0282325 A1 | 11/2011 | Gregory |
| 2012/0027867 A1 | 2/2012 | Fischer et al. |
| 2012/0103536 A1 | 5/2012 | Hubbard et al. |
| 2012/0167405 A1 | 7/2012 | Hubbard et al. |
| 2012/0222326 A1 | 9/2012 | Hubbard et al. |
| 2013/0000774 A1 | 1/2013 | Rosiello |
| 2013/0048225 A1 | 2/2013 | Hubbard et al. |
| 2013/0056158 A1 | 3/2013 | Hubbard et al. |
| 2013/0126101 A1 | 5/2013 | Hubbard, Jr. et al. |
| 2013/0129817 A1 | 5/2013 | Consigny |
| 2013/0209985 A1 | 8/2013 | Hoke |
| 2013/0243877 A1 | 9/2013 | Haley |
| 2013/0264288 A1 | 10/2013 | Hlavinka et al. |
| 2014/0083627 A1 | 3/2014 | Khan et al. |
| 2014/0083628 A1 | 3/2014 | Khan et al. |
| 2014/0088768 A1 | 3/2014 | Haley et al. |
| 2014/0221873 A1 | 8/2014 | Hayakawa et al. |
| 2014/0230266 A1 | 8/2014 | Luy et al. |
| 2015/0099866 A1 | 4/2015 | Kelleher |
| 2015/0158652 A1 | 6/2015 | Root et al. |
| 2015/0354894 A1 | 12/2015 | Corbin, III et al. |
| 2016/0015863 A1 | 1/2016 | Gupta et al. |
| 2016/0082043 A1 | 3/2016 | Khan et al. |
| 2016/0082044 A1 | 3/2016 | Liu |
| 2016/0084572 A1 | 3/2016 | Khan et al. |
| 2016/0113965 A1 | 4/2016 | DaCorta et al. |
| 2016/0223255 A1 | 8/2016 | Beetz |
| 2016/0362307 A1 | 12/2016 | Shiner |
| 2017/0100339 A1 | 4/2017 | Liu et al. |
| 2017/0113824 A1 | 4/2017 | Root et al. |
| 2017/0203871 A1 | 7/2017 | Murto et al. |
| 2017/0259186 A1 | 9/2017 | Khan et al. |
| 2017/0367322 A1 | 12/2017 | Liu et al. |
| 2018/0128544 A1 | 5/2018 | Corbin et al. |
| 2018/0153811 A1 | 6/2018 | Fischer et al. |
| 2018/0207654 A1 | 7/2018 | Phua |
| 2018/0229150 A1 | 8/2018 | Sorensen |
| 2019/0106254 A1 | 4/2019 | Weimer et al. |
| 2019/0223671 A1 | 7/2019 | Tomasiak |
| 2019/0241300 A1 | 8/2019 | Root et al. |
| 2019/0255455 A9 | 8/2019 | Sorensen |
| 2019/0298765 A1 | 10/2019 | DaCorta et al. |
| 2020/0022691 A1 | 1/2020 | Pollack |
| 2020/0298137 A9 | 9/2020 | Khan |
| 2021/0069607 A1 | 3/2021 | Khan et al. |
| 2021/0213057 A1 | 7/2021 | DaCorta et al. |
| 2021/0290545 A1 | 9/2021 | Lie et al. |
| 2022/0040110 A1 | 2/2022 | Lie et al. |
| 2022/0106357 A1 | 4/2022 | Patatanyan |
| 2023/0172849 A1 | 6/2023 | Zeki |
| 2024/0109000 A1 | 4/2024 | Liu |
| 2024/0131062 A1 | 4/2024 | Popovsky |
| 2024/0131236 A1 | 4/2024 | LaRocque |
| 2024/0131446 A1 | 4/2024 | Andrews |
| 2024/0159462 A1 | 5/2024 | Andrews |
| 2024/0191943 A1 | 6/2024 | Andrews |

FOREIGN PATENT DOCUMENTS

| | | |
|---|---|---|
| CA | 1182411 A | 2/1985 |
| CA | 2065582 | 10/1992 |
| CA | 2065582 A1 | 10/1992 |
| CA | 2 472 028 | 8/2003 |
| CA | 2757961 | 10/2010 |
| CA | 2816090 A1 | 5/2012 |
| CH | 622683 | 4/1981 |
| CH | 622683 A5 | 4/1981 |
| CN | 1315139 | 10/2001 |
| CN | 1315139 A | 10/2001 |
| CN | 102206273 A | 10/2011 |
| CN | 108005711 A | 5/2018 |
| CN | 111789867 B | 1/2022 |
| DE | 3507278 | 9/1986 |
| EP | 0058903 | 9/1982 |
| EP | 0058903 A1 | 9/1982 |
| EP | 0408801 A1 | 1/1991 |
| EP | 1050220 A1 | 8/2000 |
| EP | 1050220 | 11/2000 |
| EP | 2745922 A2 | 6/2014 |
| EP | 2745923 A2 | 6/2014 |
| EP | 2416790 | 5/2018 |
| EP | 3151662 B1 | 10/2020 |
| GB | 573500 | 11/1945 |
| GB | 886533 | 1/1962 |
| GB | 964367 | 7/1964 |
| GB | 975786 | 11/1964 |
| GB | 1188168 | 4/1970 |
| GB | 2003042 | 3/1979 |
| GB | 2003042 A | 3/1979 |
| HK | 1167098 | 8/2012 |
| JP | 6011903 | 2/1981 |
| JP | 56011903 | 2/1981 |
| JP | 3218201 | 9/1988 |
| JP | 63218201 | 9/1988 |
| JP | 1011618 | 1/1989 |
| JP | 3131302 | 6/1991 |
| JP | 3181301 | 8/1991 |
| JP | 525910 | 2/1993 |
| JP | 5245301 | 9/1993 |
| JP | 5252910 | 10/1993 |
| JP | 10182124 | 7/1998 |
| JP | H10182124 A | 7/1998 |
| JP | 3219828 B2 | 10/2001 |
| JP | 2002009037 | 1/2002 |
| JP | 2005191275 | 7/2005 |
| JP | 2005191275 A | 7/2005 |
| JP | 2007216158 | 8/2007 |
| JP | 2007216158 A | 8/2007 |
| JP | 6336419 | 6/2018 |
| KR | 911657 B1 | 8/2009 |
| KR | 2022079809 A | 6/2022 |
| MX | 2011010633 | 1/2012 |
| WO | 1996015849 | 5/1996 |
| WO | WO1996015849 A1 | 5/1996 |
| WO | 1996018312 | 6/1996 |
| WO | WO1996018312 A1 | 6/1996 |
| WO | 1997038578 | 10/1997 |
| WO | WO1997038578 A1 | 10/1997 |
| WO | 1999007236 | 2/1999 |
| WO | 1999007390 | 2/1999 |
| WO | WO1999007236 A1 | 2/1999 |
| WO | WO1999007390 A1 | 2/1999 |
| WO | 2000056166 | 9/2000 |
| WO | WO2000056166 A1 | 9/2000 |
| WO | 2001072141 | 10/2001 |
| WO | WO2001072141 A2 | 10/2001 |
| WO | 2002078741 | 10/2002 |
| WO | 2002078742 | 10/2002 |
| WO | WO2002078741 A2 | 10/2002 |
| WO | WO2002078742 A2 | 10/2002 |
| WO | WO2002083157 A1 | 10/2002 |
| WO | 2002092213 | 11/2002 |
| WO | WO2002092213 A1 | 11/2002 |
| WO | 2003030654 | 4/2003 |
| WO | 2003030918 | 4/2003 |
| WO | WO2003030654 A1 | 4/2003 |

(56) References Cited

FOREIGN PATENT DOCUMENTS

| WO | WO2003030918 A1 | 4/2003 |
|---|---|---|
| WO | WO-03037303 A | 5/2003 |
| WO | 2003063607 | 8/2003 |
| WO | WO2003063607 A1 | 8/2003 |
| WO | 2004057962 | 7/2004 |
| WO | 2004075988 | 9/2004 |
| WO | WO2004075988 A2 | 9/2004 |
| WO | WO2004078187 A1 | 9/2004 |
| WO | WO2005079755 A2 | 9/2005 |
| WO | 2007036227 | 4/2007 |
| WO | WO2007036227 A1 | 4/2007 |
| WO | WO-2008080167 A2 | 7/2008 |
| WO | 2008122288 | 10/2008 |
| WO | WO2008122288 A1 | 10/2008 |
| WO | WO2008143769 A1 | 11/2008 |
| WO | WO2010111132 A2 | 9/2010 |
| WO | 2010117976 | 10/2010 |
| WO | WO2010113632 A1 | 10/2010 |
| WO | WO2010117976 A1 | 10/2010 |
| WO | WO2011075614 A2 | 6/2011 |
| WO | WO2012058575 A3 | 5/2012 |
| WO | WO2013141050 A1 | 9/2013 |
| WO | WO2016036807 A1 | 3/2016 |
| WO | WO2016208675 A1 | 12/2016 |
| WO | WO2019074886 A1 | 4/2019 |
| WO | WO-2020065413 A1 | 4/2020 |
| WO | WO2020111132 A1 | 6/2020 |
| WO | WO2024059759 A1 | 3/2024 |
| WO | WO2024059762 A1 | 3/2024 |
| WO | WO2024059763 A1 | 3/2024 |
| WO | WO2024059764 A1 | 3/2024 |
| WO | WO2024059765 A1 | 3/2024 |
| WO | WO2024059766 A1 | 3/2024 |
| WO | WO2024059767 A1 | 3/2024 |
| WO | WO2024059768 A1 | 3/2024 |
| WO | WO2024059769 A1 | 3/2024 |
| WO | WO2024059770 | 3/2024 |
| WO | WO2024059771 A1 | 3/2024 |
| WO | WO2024059772 A1 | 3/2024 |
| WO | WO2024059774 A1 | 3/2024 |

OTHER PUBLICATIONS

Shuja et al., Development and Testing of Freeze-Dried Plasma for the Treatment of Trauma-Associated Coagulopathy, The Journal of Trauma Injury, Infection and Critical Care, Presented at the 38th Annual Meeting of the Western Trauma Association, Feb. 24-Mar. 1, 2008, vol. 65, pp. 975-985.
Solheim B G et al., Improved Preservation of Coagulation Factors After Pre-Storage Leukocyte Depletion of Whole Blood; Transfus Apher Sci., Oct. 29, 2003.(2): pp. 133-139.
Goto et al., Characterization of the Unique Mechanism Mediating the Shear-dependent Binding of Soluble von Willebrand Factor to Platelets, The Journal of Biological Chemistry, vol. 270, No. 40, Oct. 6, 1995, pp. 23352-23361, 1995.
Horn, R.G., Addition of a polarizing microscope to the Weissenberg Rheogoniometer, 1979 American Institute of Physics, Rev. Sci. Instrum. 50(50, May 1979, pp. 659-661.
Moake, et al., Involvement of Large Plasma von Willebrand Factor (VWF) Multimers and Unusually Large vWF Forms Derived from Endothelial Cells in Shear Stress-induced Platelet Aggregation, The American Society for Clinical Investigation, Inc., vol. 78, Dec. 1986, pp. 1456-1461.
Mini Spray Dryer B-290; Application Note; www.buchi.com; Mar. 30, 2008.
Nano Spray Dryer B-90; www.buchi.com; Jul. 18, 2011.
Lea, et al. "The Reaction between Proteins and Reducing Sugars in the "Dry" State" Department of Pathology, University of Cambridge; Jun. 5, 1950; pp. 626-629.
Carpenter, et al. "Rational Design of Stable Lyophilized Protein Formulations: Theory and Practice" Kluwer Academic/Plenum Publishers; 2002; pp. 109-133.
Schmid "Spray drying of protein precipitates and Evaluation of the Nano Spray Dryer B-90" PhD Thesis; 2011; 125 pages.
Shuja, et al. "Development and Testing of Low-Volume Hyperoncotic, Hyperosmotic Spray-Dried Plasma for the treatment of Trauma-Associated Coagulopathy" The Journal of Trauma; Mar. 2011; vol. 70; No. 3; pp. 664-671.
Bakaltcheva; et al. "Freeze-dried whole plasma: Evaluating sucrose, trehalose, sorbitol, mannitol and glycine as stabilizers" Thrombosis Research; 2007; vol. 120; pp. 105-116.
European Search Report, EP Application No. 14154366, mailed Aug. 29, 2014, pp. 1-3.
European Search Opinion, EP Application No. 14154366, mailed Aug. 29, 2014, pp. 1-3.
International Search Report and Written Opinion, PCT/US2010/049176, mailed Nov. 4, 2010, pp. 1-10.
International Search Report and Written Opinion, PCT/US2011/058358, mailed Jul. 4, 2012, pp. 1-9.
Answer, Affirmative Defenses, Counterclaims, Cross-Claims and Jury Demand, *Entegrion, Inc.* vs *Velico Medical, Inc.*, dated Dec. 3, 2012, pp. 1-47.
Civil Action Cover Sheet; *Entegrion, Inc.* vs *Velico Medical, Inc.*, dated Oct. 19, 2012, pp. 1-2.
Complaint including Exhibit A, B, and C; *Entegrion, Inc.* vs *Velico Medical, Inc.*, dated Oct. 19, 2012, pp. 1-29.
Mini Spray Dryer B-290—Application Note; www.buchi.com; Mar. 30, 2008, entire document; 1 page.
Nano Spray Dryer B-90; www.buchi.com; Jul. 18, 2011, entire document, 12 pages.
Mini Spray Dryer System Configuration; www.buchi.com; Jan. 8, 2007, entire document, 1 page.
Quick Operation Guide; Mini Spray Dryer B-290; www.buchi.com; Sep. 16, 2004, pp. 15-53.
Process Parameters; www.buchi.com; Nov. 21, 2008, pp. 1-2.
Training Papers Spray Drying; Version B; www.buchi.com; 19 pages; Oct. 29, 2002.
Mini Spray Dryer B-290; www.buchi.com; May 10, 2007, pp. 1-8.
Fischer M., et al., "Stability of African swine fever virus on spiked spray-dried porcine plasma," *Transboundary and Emerging Diseases*, 68(5): 2806-2811 (2021).
International Preliminary Report on Patentability, PCT/US2011/058358, mailed Apr. 30, 2013, pp. 1-7.
Edwards et al., The Preparation and Use of Dried Plasma for Transfusion; British Medical journal; vol. 1, No. 4131;Mar. 9, 1940; pp. 377-381.
Blazquez, E., et al., "Biosafety steps in the manufacturing process of spray-dried plasma: a review with emphasis on the use of ultraviolet irradiation as a redundant biosafety procedure," *Porcine Health Management*, 6(16): p. 78 refs. (2020), 9 pages.
Blazquez, E., et al., "Effect of spray-drying and ultraviolet C radiation as biosafety steps for CSFV and ASFV inactivation in porcine plasma," *PLoS One*, 16(4) (2021) , entire document, 11 pages.
Entegrion's Reply To Counterclaims; *Entegrion, Inc.* vs *Velico Medical, Inc;* Dated: Jan. 14, 2013, entire document, 22 pages.
Entegrion's Motion to Dismiss Counts I, Ii, V, Vi and XI of Velico Medical, Inc's Counterclaims and Memorandum in Support of Entegrion's Motion To Dismiss Counts I, II, V, Vi, and XI of Velico Medical, Inc.'s Counterclaims; *Entegrion, Inc.* vs *Velico Medical, Inc;* Dated: Jan. 14, 2013, entire document, 3 pages.
International Preliminary Report on Patentability, PCT/US2010/049176, mailed Feb. 18, 2014, pp. 1-9.
Pusateri, Anthony E."Dried plasma: state of the science and recent developments" *Transfusion* 56: S128-S139 (Apr. 2016).
Pusateri, Anthony E."Comprehensive US government program for dried plasma development" *Transfusion* 56: S16-S23 (2016).
Popovsky, Mark A. "Spray-dried plasma: A post-traumatic blood "bridge" for life-saving resuscitation" *Transfusion*. 2021;61:S294-S300 (2021).
Flaumenhaft, Elissa J. et al., "Retention of Coagulation Factors and Storage of Freeze-Dried Plasma," *Military Med.* 186 (S1):400-407 (2021).

(56) References Cited

OTHER PUBLICATIONS

Parr, Ashely, "Coagulation Activity of Freeze-Dried Plasma is similar to that of Fresh Frozen Plasma" (May 16, 2018) entire document, 14 pages.
Peng, Henry T. "Ex vivo hemostatic and immune-inflammatory profiles of freeze-dried plasma" Transfusion 61: S119-S130 (2021).
Larry J. Dumont, et al, "The bioequivalence of frozen plasma prepared from whole blood held overnight at room temperature compared to fresh-frozen plasma prepared within eight hours of collection," *Transfusion* 55: 480 (2015), entire document, 9 pages.
Blazquez, E., et al., "Combined effects of spray-drying conditions and postdrying storage time and temperature on *Salmonella choleraesuis* and *Salmonella typhimurium* survival when inoculated in liquid porcine plasma," *Letters in Applied Microbiology*, 67(2): 205-211 (2018).
S. Suessner, et al., "Comparison of several complement and coagulation factor concentrations in different plasma products." *Transfusion Medicine and Hemotherapy*, 41 (supplement 1) Abstract No. PBK-V02: p. 36 (2014), 3 pages.
Cancelas, J. A., "A Phase 1, Single-Center, Partial Double-blind, Randomized, Controlled (Versus Fresh Frozen Plasma [FFP] In Cohort 3 Only) Clinical Study Of The Safety Of Ascending Doses Of Autologous Freeze Dried Plasma (FDP) In Healthy Volunteers," Falls Church, VA: The Surgeon General, Department of the Army (2018), p. 1-128.
Polo, J., et al., "Neutralizing antibodies against porcine circovirus type 2 in liquid pooled plasma contribute to the biosafety of commercially manufactured spray-dried porcine plasma," *Journal of Animal Science*, 91(5): 2192-2198 (2013).
Blazquez, E., et al., "UV-C irradiation is able to inactivate pathogens found in commercially collected porcine plasma as demonstrated by swine bioassay," *Veterinary Microbiology*, 239 (2019), entire document, 2 pages.
Blazquez, E., et al., "Evaluation of the effectiveness of the SurePure Turbulator ultraviolet-C irradiation equipment on inactivation of different enveloped and non-enveloped viruses inoculated in commercially collected liquid animal plasma," PLoS One, 14(2) (2019), entire document, 17 pages.
Shen, E., et al., "Commercially produced spray-dried porcine plasma contains increased concentrations of porcine circovirus type 2 DNA but does not transmit porcine circovirus type 2 when fed to naïve pigs," *Journal of Animal Science*, 89(6): 1930-1938 (2011).
Pujols, J., and Segales, J., "Survivability of porcine epidemic diarrhea virus (PEDV) in bovine plasma submitted to spray drying processing and held at different time by temperature storage conditions," *Veterinary Microbiology*, 174(3/4): 427-432 (2014).
Blazquez, E., et al., "Evaluation of ultraviolet-C and spray-drying processes as two independent inactivation steps on enterotoxigenic *Escherichia coli* K88 and K99 strains inoculated in fresh unconcentrated porcine plasma," *Letters in Applied Microbiology*, 67(5): 442-448 (2018).
Pujols, J., et al., "No transmission of hepatitis E virus in pigs fed diets containing commercial spray-dried porcine plasma: a retrospective study of samples from several swine trials," *Virology Journal*, 11: pp. 232 (2014), 8 pages.
Foddai, A., et al., "Probability of introducing porcine epidemic diarrhea virus into Danish pig herds by imported spray-dried porcine plasma," *Porcine Health Management*, 1: p. 18 (2015), 11 pages.
Gerber, P. F., et al., "The spray-drying process is sufficient to inactivate infectious porcine epidemic diarrhea virus in plasma," *Veterinary Microbiology*, 174(1/2): 86-92 (2014).
Patterson, A. R., et al., "Efficacy of experimentally produced spray-dried plasma on infectivity of porcine circovirus type 2," *Journal of Animal Science*, 88(12): 4078-4085 (2010).
Pujols, J., et al., "Commercial spray-dried porcine plasma does not transmit porcine circovirus type 2 in weaned pigs challenged with porcine reproductive and respiratory syndrome virus," *Veterinary Journal*, 190(2): 16-20 (2011).

Blazquez, E., et al., "Ultraviolet (UV-C) inactivation of Enterococcus faecium, *Salmonella choleraesuis* and *Salmonella typhimurium* in porcine plasma," *PLoS One*, 12(4) (2017), 11 pages.
Polo, J., et al., "Ultraviolet Light (UV) Inactivation of Porcine Parvovirus in Liquid Plasma and Effect of UV Irradiated Spray Dried Porcine Plasma on Performance of Weaned Pigs," *PLoS One*, 10(7) (2015), 12 pages.
Pujols, J., et al., "Lack of transmission of porcine circovirus type 2 to weanling pigs by feeding them spray-dried porcine plasma," *Veterinary Record*, 163(18): 536-538 (2008).
Opriessnig, T., et al., "Porcine Epidemic Diarrhea Virus RNA Present in Commercial Spray-Dried Porcine Plasma Is Not Infectious to Naïve Pigs," *PLoS One*, 9(8) (2014), 10 pages.
Polo, J., et al., "Efficacy of spray-drying to reduce infectivity of pseudorabies and porcine reproductive and respiratory syndrome (PRRS) viruses and seroconversion in pigs fed diets containing spray-dried animal plasma," *Journal of Animal Science*, 83(8): 1933-1938 (2005).
Perez-Bosque, A., et al., "Spray dried plasma as an alternative to antibiotics in piglet feeds, mode of action and biosafety," *Porcine Health Management*, 2: p. 16 (2016) 10 pages.
Moreto, M., et al., "Dietary supplementation with spray-dried porcine plasma has prebiotic effects on gut microbiota in mice," *Scientific Reports*, 10(1): p. 2926 (2020), 13 pages.
Hulst, M. M., et al., "Study on inactivation of porcine epidemic diarrhoea virus, porcine sapelovirus 1 and adenovirus in the production and storage of laboratory spray-dried porcine plasma," *Journal of Applied Microbiology*, 126(6): 1931-1943 (2019).
Pasick, J., et al., "Investigation into the Role of Potentially Contaminated Feed as a Source of the First-Detected Outbreaks of Porcine Epidemic Diarrhea in Canada," *Transboundary and Emerging Diseases*, 61(5): 397-410 (2014).
Duffy, M. A., et al., "Impact of dietary spray-dried bovine plasma addition on pigs infected with porcine epidemic diarrhea virus," *Translational Animal Science*, 2(4): 349-357 (2018).
Cottingim, K. M., et al., "Ultraviolet irradiation of spray-dried porcine plasma does not affect the growth performance of nursery pigs when compared with nonirradiated bovine plasma," *Journal of Animal Science*, 95(7): 3120-3128 (2017).
Gebhardt, J. T., et al., "Determining the impact of commercial feed additives as potential porcine epidemic diarrhea virus mitigation strategies as determined by polymerase chain reaction analysis and bioassay," *Translational Animal Science*, 3(1): 28-37 (2019).
Champagne C. P., et al., "Effect of bovine colostrum, cheese whey, and spray- dried porcine plasma on the in vitro growth of probiotic bacteria and *Escherichia coli*," *Canadian Journal of Microbiology*, 60(5): 287-295 (2014).
Perez-Bosque, A., et al., "The Anti-Inflammatory Effect of Spray-Dried Plasma Is Mediated by a Reduction in Mucosal Lymphocyte Activation and Infiltration in a Mouse Model of Intestinal Inflammation," *Nutrients*, 8(10) (2016), p1-13.
Prabhu, B., et al., "Effects of spray-dried animal plasma on the growth performance of weaned piglets—A review," *Journal of Animal Physiology and Animal Nutrition*, 105(4): 699-714 (2021).
Santos, D., et al., "Spray Drying: An Overview," *Biomaterials*, (2017), p. 1-29.
USAMRMC military plasma article "Advanced Development Products," (Second Edition). U.S. Army Medical Research and Materiel Command (2017), p. 521-529.
GovTribe, "Definitive Contract H9222216C0081", [online], [retrieved on Mar. 20, 2020], Retrieved from https://govtribe.com/award/federal-contract-award/definitive-contract-h9222216c0081, entire document, 3 pages.
Noorman, F. et al. "Lyophilized Plasma, an Alternative to 4 degrees C Stored Thawed Plasma for the Early Treatment of Trauma Patients with (Massive) Blood Loss in Military Theatre," *Transfusion* 55A (2012), p. 1-2.
Bux, J., et al., "Quality of freeze-dried (lyophilized) quarantined single-donor plasma," *Transfusion*, 53: 3203-3209 (2013).
Noorman, F., "Comparison of a single Spray dried plasma product with standard Sanquin and MBB frozen, thawed (coldstored) plasma," (Final Report). Utrecht, Netherlands: Military Blood Bank (2021), p. 1-7.

(56) References Cited

OTHER PUBLICATIONS

Sailliol, A., et al., "The evolving role of lyophilized plasma in remote damage control resuscitation in the French Armed Forces Health Service," *Transfusion*, 53: 65S-71S (2013).
Zaza, M., et al. "Dried Plasma," *Damage Control Resuscitation: Identification and Treatment of Life-Threatening Hemorrhage*, 145-162 (2019).
Wataha, K., et al., "Spray-dried plasma and fresh frozen plasma modulate permeability and inflammation in vitro in vascular endothelial cells," *Transfusion*, 53: 80S-90S (2013).
Wang, H.H., et al., "Effect of gallbladder hypomotility on cholesterol crystallization and growth in CCK-deficient mice," *Biochim Biophys Acta*, 1801(2): 138-146 (2010).
Gadeela, N., et al., "The Impact of Circulating Cholesterol Crystals on Vasomotor Function. Implications for No-Reflow Phenomenon," *J Am Coll Cardiol Int*, 4: 521-529 (2011).
Abela, G.S., et al., "The Effect of Ethanol on Cholesterol Crystals During Tissue Preparation for Scanning Electron Microscopy," *J Am Coll Cardiol* 1: 93 (2012), 1 page.
Li, H., et al., "Synthesis of β-cyclodextrin conjugated superparamagnetic iron oxide nanoparticles for selective binding and detection of cholesterol crystals," *Chem Commun*, 48(28): 3385-3387 (2012).
Elizabeth, A., et al., "Growth and micro-topographical studies of gel grown cholesterol crystals," *Bull Mater Sci*, 24(4): 431-434 (2001).
Kroll, M.H., et al., "Effect of Lyophilization on Results of Five Enzymatic Methods for Cholesterol," *Clin Chem*, 35(7): 1523-1526 (1989).
Mughal, M.M., et al., "Symptomatic and asymptomatic carotid artery plaque," *Expert Rev Cardiovasc Ther*, 9(10): 1315-1330 (2011).
Morales, J., and Gonzalez, E., "Cholesterol Crystal Embolization," *Blood Purif*, 24: 431-432 (2006).
Walton, T.J., et al., "Systemic cholesterol crystal embolisation with pulmonary involvement: a fatal combination after coronary angiography," *Postgrad Med J*, 78: 288-289 (2002).
Oe, K., et al., "Late Onset of Cholesterol Crystal Embolism after Thrombolysis for Cerebral Infarction," *Inter Med*, 49: 833-836 (2010).
Warren, B. A., and Vales, O., "The ultrastructure of the stages of atheroembolic occlusion of renal arteries," *Br J Exp Pathol*, 54(5): 469-478 (1973).
Warren B. A., Vales, O., "Electron microscopy of the sequence of events in the atheroembolic occlusion of cerebral arteries in an animal model," *Br J Exp Pathol*, 56(3):205-215 (1975).
Warren, B. A., and Vales, O., "The ultrastructure of the reaction of arterial walls to cholesterol crystals in atheroembolism," *Br J Exp Pathol*, 57(1), 67-77 (1976).
Steiner, T.J., et al., "Cholesterol crystal embolization in rat brain: a model for atheroembolic cerebral infarction," *Stroke*, 11: 184-189 (1980).
Nozari A., et al., "Microemboli may link spreading depression, migraine aura, and patent foramen ovale," *Ann Neurol*, 67(2):221-229 (2010).
Duewell, P., et al., "NLRP3 inflammasomes are required for atherogenesis and activated by cholesterol crystals," *Nature*, 464,7293: 1357-1361 (2010).
Samstadt, E. O., et al., "Cholesterol crystals induce complement-dependent inflammasome activation and cytokine release," *J Immunol*, 192(67): 2837-2845 (2014).
Grebe, A., and Latz, E., "Cholesterol Crystals and Inflammation," *Curr Rheumatol Rep*, 15: 313 (2013) 7 pages.
Sheedy, F., et al., "CD36 coordinates NLRP3 inflammasome activation by facilitating intracellular nucleation of soluble ligands into particulate ligands in sterile inflammation," *Nat Immunol*, 14: 812-820 (2013).
Ness, M. V., et al., "Neutrophils Contain Cholesterol Crystals in Transfusion-Related Acute Lung Injury (TRALI)," *Am J Clin Pathol*, 140(2): 170-176 (2013).
Sheffield, W. P., et al., "Retention of hemostatic and immunological properties of frozen plasma and COVID-19 convalescent apheresis fresh-frozen plasma produced and freeze-dried in Canada," *Transfusion*, 62: 418-428 (2021).
Garrigue, D., et al., "French lyophilized plasma versus fresh frozen plasma for the initial management of trauma-induced coagulopathy: a randomized open-label trial," *J Thrombosis and Haemostasis*, 16:481-489 (2017).
Van, P. Y., et al., "Lyophilized Plasma Reconstituted With Ascorbic Acid Suppresses Inflammation and Oxidative DNA Damage," *J Trauma*, 71(1):20-24 (2011).
Medical Countermeasures, "BARDA continues partnership with Velico Medical for development of their FrontlineODP spray-dry plasma system to prepare for a radiological or nuclear emergency," [online], [retrieved on Sep. 20, 2021], Retrieved from https://www.medicalcountermeasures.gov/newsroom/2021/velico-medical/ entire document, 20 pages.
Burnouf, T., et al., "Assessment of complement activation during membrane-based plasmapheresis procedures," *J Clin Apheresis*, 19: 142-147 (2004).
Ohta, R., et al., "Serum concentrations of complement anaphylatoxins and proinflammatory mediators in patients with 2009 H1N1 influenza," *Microbiology and Immunology*, 55: 191-198 (2011).
"French Lyophilised Plasma (FLYP)," Ministry of Defence, Armed Forces Health Service, Jean Julliard Armed Forces Blood Transfusion Service (Technical Notice and Summary of Product Characteristics) (2013), 2 pages.
Arun, R., "Freeze Dried Plasma Role in Emergency Resuscitation", Tirupati, India: Sri Venkateswara Institute of Medical Sciences, https://www.istm.net.in/transmedcon2016-presentations/99.%20Freeze%20Dried%20Plasma-Role%20in%20Emergency%20Resucitation.pdf, downloaded on Jan. 16, 2021, entire document, 51 pages.
Pusateri, A.E., and Weiskopf, R.B. "Dried Plasma for Trauma Resuscitation," *Trauma Induced Coagulopathy*, 705-718 (2021).
Sunde, G.A., "Prehospital Plasma / TXA experience—FDP in Norwegian HEMS," Norway: Norsk Luftambulanse (2014), p. 1-24.
Acker, J. P., et al., "Quality Assessment of Established and Emerging Blood Components for Transfusion," *Journal of Blood Transfusion*, (2016) p. 1-29.
Warr, M., "Lyoplas reconstitution English," Deutsches Rotes Kreuz, [Youtube], [retrieved on Jan. 9, 2022], Retrieved from https://www.youtube.com/watch?v=PdydStEygtk. Entire document.
"LyoPlas N—w A freeze-dried single donor plasma," Brochure, DRK—Blutspendedienst West, Hagen, Germany: Deutsches Rotes Kreuz (May 2012), entire document, 14 pages.
Mew, I., "Reconstituting Lyoplas (Freeze dried FFP)", [Youtube], [retrieved on Jan. 9, 2022], Retrieved from https://www.youtube.com/watch?v=RXpQDMwVK8Y. ), entire document, 9 pages.
Cancelas, J. A., et al., "Characterization and first-in-human clinical dose-escalation safety evaluation of a next-gen human freeze-dried plasma," *Transfusion*, 62: 406-417 (2021).
"Mirasol Pathogen Reduction Technology System", TerumoBCT (2012), entire document, 13 pages.
Terumo BCT, "Terumo BCT Awarded $1.9 Million from the United States Government to Support Development of Freeze-Dried Plasma," [online], [retrieved on Mar. 20, 2020], Retrieved from https://www.terumobct.com/Pages/News/Press%20Releases/Terumo_BCT-Awarded_1$-9_Million_from_the-United_States_Government_to_Support_Development_of_Freeze-Dried_Plasma.aspx. , entire document, 2 pages.
Spinella, P. C., "Zero preventable deaths after traumatic injury: an achievable goal," *J Trauma Acute Care Surg*, 82:S2-S8 (2017).
Davis, J. S., et al., "An analysis of prehospital deaths: who can we save?," *J Trauma Acute Care Surg*, 77:213-218 (2014).
Shackelford, S. A., et al., "Association of prehospital blood product transfusion during medical evacuation of combat casualties in Afghanistan with acute and 30-day survival," *JAMA*, 318:1581-1591 (2017).
Gurney, J. M., and Spinella, P. C., "Blood transfusion management in the severely bleeding military patient," *Curr Opin Anesthesiol*, 31:207-214 (2018).
Moore, E. E., et al., "Plasma first in the field for postinjury hemorrhagic shock," *Shock*, 41(Suppl 1):35-38 (2014).

(56) References Cited

OTHER PUBLICATIONS

Maegele, M., et al., "Red-blood-cell to plasma ratios transfused during massive transfusion are associated with mortality in severe multiple injury: a retrospective analysis from the trauma registry of the deutsche Gesellshaft fur Unfallchirugerie," *Vox Sang*, 95:112-119 (2008).
Holcomb, J. B., et al., "Prehospital transfusion of plasma and red blood cells in trauma patients," *Prehosp Emerg Care*, 19:1-9 (2015).
Holcomb, J. B., et al., "The prospective, observational, multicenter major trauma transfusion (PROMMTT) study: comparative effectiveness of a time-varying treatment with competing risks," *JAMA Surg*, 148:127-136 (2013).
Holcomb, J. B., et al., "Damage control resuscitation: directly addressing the early coagulopathy of trauma," *J Trauma Acute Care Surg*, 62:307-310 (2007).
Holcomb, J. B., et al., "Transfusion of plasma, platelets, and red blood cells in a 1:1:1 vs 1:1:2 ratio and mortality in patients with severe trauma: the PROPPR randomized clinical trial," *JAMA*, 313:471-482 (2015).
Sperry, J. L., et al., "Prehospital plasma during air medical transport in trauma patients at risk for hemorrhagic shock," *N Engl J Med*, 379:315-326 (2018).
Zink, K. A., et al., "A high ratio of plasma and platelets to packed red blood cells in the first 6 hours of massive transfusion improves outcomes in a large multicenter study," *Am J Surg*, 197:565-570 (2009).
Saillol, A., et al., "The evolving role of lyophilized plasma in remote damage control resuscitation in the French armed forces health service," *Transfusion*, 53(Suppl 1): S129-S39 (2013).
Nuguyen, C., et al., "Use of French lyophilized plasma transfusion in severe trauma patients is associated with an early plasma transfusion and early transfusion ratio improvement," *J Trauma Acute Care Surg*, 84:780-785 (2018).
Shlaifer, A., et al., "Prehospital administration of freeze-dried plasma, is it the solution for trauma casualties?," *J Trauma Acute Care Surg*, 83:675-682 (2017).
Shlaifer, A., et al., "The impact of prehospital administration of freeze-dried plasma on casualty outcome," *J Trauma Acute Care Surg*, 86:108-115 (2019).
Bjerkvig, C.K., et al., ""Blood failure" time to view blood as an organ: how oxygen debt contributes to blood failure and its implications for remote damage control resuscitation," *Transfusion*, 56(Suppl 2):S182-S189 (2016).
White, N. J., et al., "Hemorrhagic blood failure: oxygen debt, coagulopathy, and endothelial damage," *J Trauma Acute Care Surg*, 82(6S Suppl 1):S41-S49 (2017).
Aird, W. C., "Endothelium and haemostasis," *Hamostaseologie*, 35:11-16 (2015).
Esmon, C. T., "Inflammation and the activated protein C anticoagulant pathway," *Semin Thromb Hemost*, 32(Suppl 1):49-60 (2006).
Tuma, M., et al., "Trauma and endothelial glycocalyx: the microcirculation helmet?," *Shock*, 46:352-357 (2016).
Kozar, R. A., and Pati, S., "Syndecan-1 restitution by plasma after hemorrhagic shock," *J Trauma Acute Care Surg*, 78(6 Suppl 1):S83-S86 (2015).
Rahbar, E., et al., "Endothelial glycocalyx shedding and vascular permeability in severely injured trauma patients," *J Transl Med*, 13:117 (2015), entire document, 7 pages.
Johansson, P. I., et al., "Traumatic Endotheliopathy: a prospective observational Study of 424 severely injured patients," *Ann Surg*, 265:597-603 (2017).
Wu, F., et al., "miR-19b targets pulmonary endothelial syndecan-1 following hemorrhagic shock," *Sci Rep*, 10:15811 (2020), 10 pages.
Johansson, P. I., et al., "Shock induced endotheliopathy (SHINE) in acute critical illness—a unifying pathophysiologic mechanism," *Crit Care*, 21:25 (2017), 7 pages.
Spronk, H. M., et al., "New insights into modulation of thrombin formation," *Curr Atheroscler Rep*, 15:363 (2013), 9 pages.
Dunbar, N. M., and Chandler, W. L., "Thrombin generation in trauma patients," *Transfusion*, 49:2652-2660 (2009).
Chandler, W. L., "Procoagulant activity in trauma patients," *Am J Clin Pathol*, 134:90-96 (2010).
Cardenas, J. C., et al., "Measuring thrombin generation as a tool for predicting hemostatic potential and transfusion requirements following trauma," *J Trauma Acute Care Surg*, 77:839-845 (2014).
Rourke, C., et al., "Fibrinogen levels during trauma hemorrhage, response to replacement therapy, and association with patient outcomes," *J Thromb Haemost*, 10:1342-1351 (2012).
Raza, I., et al., "The incidence and magnitude of fibrinolytic activation in trauma patients," *J Thromb Haemost*, 11:307-314 (2013).
Hayakawa, M., et al., "Disseminated intravascular coagulation at an early phase of trauma is associated with consumption coagulopathy and excessive fibrinolysis both by plasmin and neutrophil elastase," *Surgery*, 149:221-230 (2011).
Kaplan, A. P., and Ghebrehiwet, B., "The plasma bradykinin-forming pathways and its interrelationships with complement," *Mol Immunol*, 47:2161-2169 (2010).
Omar, M. N., Mann, K. G., "Inactivation of factor Va by plasmin," *J Biol Chem*, 262:9750-9755 (1987).
Marcos-Contreras, O. A., et al., "Hyperfibrinolysis increases blood-brain barrier permeability by a plasmin- and bradykinin-dependent mechanism," *Blood*, 128:2423-2434 (2016).
Chapman, M. P., et al., "Overwhelming tPA release, not PAI-1 degradation, is responsible for hyperfibrinolysis in severely injured trauma patients," *J Trauma Acute Care Surg*, 80:16-25 (2016).
Cardenas, J. C., et al., "Elevated tissue plasminogen activator and reduced plasminogen activator inhibitor promote hyperfibrinolysis in trauma patients," *Shock*, 41:514-521 (2014).
Moore, H. B., et al., "Acute fibrinolysis shutdown after injury occurs frequently and increases mortality: a multicenter evaluation of 2,540 severely injured patients," *J Am Coll Surg*, 222:347-355 (2016).
Shakur, H., et al., "Effects of tranexamic acid on death, vascular occlusive events, and blood transfusion in trauma patients with significant haemorrhage (CRASH-2): a randomised, placebo-controlled trial," *Lancet*, 376:23-32 (2010).
Peng, Z., et al., "Fresh frozen plasma lessens pulmonary endothelial inflammation and hyperpermeability after hemorrhagic shock and is associated with loss of syndecan 1," *Shock*, 40:195-202 (2013).
Diebel, L. N., "Microfluidics: a high-throughput system for the assessment of the endotheliopathy of trauma and the effect of timing of plasma administration on ameliorating shock-associated endothelial dysfunction," *J Trauma Acute Care Surg*, 84:575-582 (2018).
Yu, Q., et al., "Identification of fibrinogen as a key anti-apoptotic factor in human fresh frozen plasma for protecting endothelial cells in vitro," *Shock*, 53:646-652 (2020).
Wu, F., and Kozar, R. A., "Fibrinogen protects against barrier dysfunction through maintaining cell surface syndecan-1 in vitro," *Shock*, 51:740-744 (2019).
Wu, F., et al., "Fibrinogen activates PAK1/Cofilin signaling pathway to protect endothelial barrier integrity," *Shock*, 55:660-665 (2020).
Lopez, E., et al., "Antithrombin III contributes to the protective effects of fresh frozen plasma following hemorrhagic shock by preventing syndecan-1 shedding and endothelial barrier disruption," *Shock*, 53:156-163 (2020).
Deng, X., et al., "Adiponectin in fresh frozen plasma contributes to restoration of vascular barrier function after hemorrhagic shock," *Shock*, 45:50-54 (2016).
Rizoli, S. B., et al., "Clotting factor deficiency in early trauma-associated coagulopathy," *J Trauma*, 71(5 Suppl 1):S427-S434 (2011).
Pati, S., et al., "Lyophilized plasma attenuates vascular permeability, inflammation and lung injury in hemorrhagic shock," *PLoS One*, 13:e0192363 (2018) , entire document, 13 pages.
Reineccius, G., "Flavor encapsulation, Chapter 7. Spray-drying of food flavors," United Kingdom: Taylor and Francis, 55-66 (1989).
"Considerations for the Development of Dried Plasma Products Intended for Transfusion", (Final Report). Food and Drug Administration (2019) , entire document, 9 pages.
Liu, Q. P., et al., "Single-donor spray-dried plasma," *Transfusion*, 59:707-719 (2019).

(56) References Cited

OTHER PUBLICATIONS

Meledeo, M. A., et al., "Spray-dried plasma deficient in high-molecular weight multimers of von Willebrand factor retains hemostatic properties," *Transfusion*, 59:714-722 (2019).
Buckley, L., and Gonzales, R., "Challenges to producing novel therapies-dried plasma for use in trauma and critical care," *Transfusion*, 59:837-845 (2019).
Bercovitz, R., et al., "Microfluidic analysis of thrombus formation in reconstituted whole blood samples comparing spray-dried plasma versus fresh-frozen plasma," *Vox Sang*, 116:540-546 (2020).
Spinella, P. C., et al., "All plasma products are not created equal: characterizing differences between plasma products," *J Trauma Acute Care Surg*, 78:S18-S25 (2015).
Bomey, N., "Hurricane Maria halts crucial drug manufacturing in Puerto Rico, may cause shortages," USA Today, [online], [retrieved on Oct. 20, 2017] Retrieved from https://www.usatoday.com/story/money/2017/09/22/hurricane-maria-pharmaceutical-industry-puerto-rico/692752001/ (2017), entire document, 9 pages.
Robinson, R. A., "BARDA Strategic Plan 2011-2016", Washington, D.C.: Biomedical Advanced Research and Development Authority. (2016), entire document, 20 pages.
Pusateri A.E., "Dried Plasma Development Update," Defense Health Agency (2015), entire document, 58 pages.
Downes, K. A., et al., "Serial measurement of clotting factors in thawed plasma stored for 5 days," *Transfusion*, 41: 570-570 (2001).
Runkel, S., et al., "The impact of whole blood processing and freezing conditions on the quality of therapeutic plasma prepared from whole blood," *Transfusion*, 55: 796-804 (2015).
Kelley, D., "Update on Plasma and Cryoprecipitate Transfusion," (Issue 1). *Institute for Transfusion Medicine* (2004), entire document, 2 pages.
Parsons, J. C., "Coagulation Hereditary bleeding disorders von Willebrand disease," [online], [retrieved on May 12, 2015], Retrieved from https://www.pathologyoutlines.com/topic/coagulationvonwillebranddisease.html, entire document, 5 pages.
ARUP Consult, "Von Willebrand Disease Testing," [online], [retrieved on May 12, 2015], Retrieved from https://arupconsult.com/sites/default/files/von_Willebrand_Disease_Testing_Algorithm.pdf, entire document, 1 page.
Heger, A., et al., "Biochemical quality of the pharmaceutically licensed plasma OctaplasLG® after implementation of a novel prion protein (PrPSc) removal technology and reduction of the solvent/detergent (S/D) process time," *Vox Sanguinis*, 97: 219-225 (2009).
Pusateri, A. E., et al., "Use of Dried Plasma in Prehospital and Austere Environments," *Anesthesiology*, 136: 327-335 (2022).
Pusateri, A. E., "Dried plasma: state of the science and recent developments," *Transfusion*, 56: S128-S139 (2016).
Chaffin, J., "Liquid Plasma," [online], [retrieved on Nov. 2, 2021], Retrieved from https://www.bbguy.org/education/glossary/gll04/, entire document, 2 pages.
Chaffin, J., "Thawed Plasma," [online], [retrieved on Nov. 2, 2021], Retrieved from https://www.bbguy.org/education/glossary/glt04/, entire document, 2 pages.
Barrows, E., "Freeze-dried Plasma The Trail Back to the Battlefield," *Defense AT&L Technology Transition*, pp. 16-19 (Sep.-Oct. 2006).
Martinaud, C., et al., "French Dried Plasma Program: Update on prehospital and emergency unit use for massive hemorrhage management," *French Military Blood Institute* (Jun. 27, 2017), entire document, 34 pages.
Martinaud, C., et al., "In Vitro Hemostatic Properties of French Lyophilized Plasma," *Anesthesiology*, 117: 339-346 (2012).
Sicard, B., et al., "Lyophilized Plasma in Out-of-Hospital Resuscitation: Risk Benefit Balance," *Ann Emerg Med*, S141:357 (2017).
Jost, D., et al., "Pre-hospital Administration of Lyophilized Plasma for Post-traumatic Coagulopathy Treatment (PREHO-PLYO)," [online], [retrieved on Apr. 25, 2022], Retrieved from https://clinicaltrials.gov/ct2/show/study/NCT02736812, entire document, 9 pages.

News 4 WOAI San Antonio, "Freeze-dried plasma saves special ops soldiers", [Youtube], [retrieved on Apr. 25, 2022], Retrieved from https://www.youtube.com/watch?v=rstOliwnwkw, entire document, 6 pages.
Lee, T., et al., "The use of lyophilized plasma in a severe multi-injury pig model," *Transfusion*, 53: 72S-79S (2013).
Holcomb, J.B., et al., "Increased Plasma and Platelet to Red Blood Cell Ratios Improves Outcome in 466 Massively Transfused Civilian Trauma Patients," *Ann Surg*, 3: 447-458 (2008).
Gatnau, R., "Spray dried porcine plasma as a source of protein and immunoglobins for weanling pigs." Unpublished master's thesis, Iowa State University, Ames, Iowa. (1990), entire document, 95 pages.
Murad, M.H., et al., "The effect of plasma transfusion on morbidity and mortality: a systematic review and meta-analysis," *Transfusion*, 50(6): 1370-1383 (2010).
Buchi Mini Spray Dryer B-191; www.buchi.com; Dec. 19, 2000, entire document, 28 pages.
DSS "Powdered Blood? Synthetic Blood Trials Show Promising Result" https://www.discoveryscientificsolutions.com/item/73 (downloaded Dec. 22, 2022), entire document, 9 pages.
Hamilton GJ "Lyophilized plasma with ascorbic acid decreases inflammation in hemorrhagic shock." J Trauma, 71 (2):292-7 (2011).
Solheim B G et al., Improved Preservation of Coagulation Factors After Pre-Storage Leukocyte Depletion of Whole Blood; Transfus Apher Sci., Oct. 2003. 29(2): pp. 133-139.
CardianBCT, Inc "Mirasol Pathogen Reduction Technology", PN 306690-148, retrieved online Apr. 4, 2023 <URL: http://eurolambda.sk/shared/files/mirasol_plasma.pdf>, 2 pages. (Year: 2009).
Terumo BCT, Inc "Mirasol Pathogen Reduction Technology System", PN 306690232, retrieved online Apr. 4, 2023 <URL: https://www.terumopenpol.com/wp-content/uploads/2019/12/306690232-1.pdf>, 7 pages. (Year: 2012).
Heger, Andrea "Frozen and Freeze-dried solvent/detergent treated plasma: Tow different pharmaceutical formations with comparable quality" Transfusion (62): pp. 2621-2630 (Sep. 11, 2022).
Highlights of Prescribing Information https://octaplasusa.com/wp-content/uploads/2021/03/20210202_pil_952_US_25.pdf Downloaded Apr. 11, 2023; Octapharma USA Inc, pp. 1-9.
Operation Manual; Mini Spray Dryer B-290; Version G; www.buchi.com; Feb. 8, 2007, pp. 1-57.
Bulut, S. et al., "Effects of Combined Shear and Thermal Forces on Destruction of *Microbacterium lacticum*" Appl Environ Microbiol, vol. 65, No. 10, pp. 4464-4469 (Oct. 1999).
International Search Report and Written Opinion, Application No. PCT/US2023/074261 pp. 1-17 (Dec. 4, 2023).
Booth, Garrett S. et al., Spray: Single-Donor Plasma Product For Room Temperature Storage, *Transfusion:* 52: 828-833 (Apr. 2012) 6 pages.
Dickey et al., "Use of Dried Plasma in Prehospital Battlefield Resuscitation Apr. 2011", Defense Technical Information Center, Aug. 8, 2011, accessible online at: https://apps.dtic.mil/sti/citations/AD1034120 (8 pages) (Aug. 8, 2011).
Butler, Frank K. "Fluid Resuscitation in Tactical Combat Casualty Care: Yesterday and Today", Wilderness & Environmental Medicine, vol. 28, Issue 2, S74-S81, Jun. 2017, DOI: https://doi.org/10.1016/j.wem.2016.12.007 (8 pages).
WayBack Machine archive of https://apps.dtic.mil/sti/citations/AD1034120, WayBack Machine, Nov. 29, 2020 (2 pages).
Semantic Scholar Web page concerning Dickey et al. "Use of Dried Plasma in Prehospital Battlefield Resuscitation", accessed by Examiner Dec. 14, 2023, U R L: https://www.semanticscholar.org/paper/Use-of-Dried-Plasma-in-Prehospital-Battlefield-Dickey/b87005a2c7cd54f022b1728a80de07df3a7f8e40 (3 pages).
International Search Report and Written Opinion, Application No. PCT/US2023/074274 pp. 1-16 (Jan. 18, 2024).
International Search Report and Written Opinion, Application No. PCT/US2023/074266, pp. 1-11 (Dec. 21, 2023).
International Search Report and Written Opinion, Application No. PCT/US2023/074265, pp. 1-17 (Feb. 6, 2024).
International Search Report and Written Opinion, Application No. PCT/US2023/074264, pp. 1-13 (Feb. 6, 2024).

(56) References Cited

OTHER PUBLICATIONS

International Search Report and Written Opinion, Application No. PCT/US2023/074267, pp. 1-12 (Feb. 6, 2024).
International Search Report and Written Opinion, Application No. PCT/US2023/074268, pp. 1-23 (Feb. 9, 2024).
International Search Report and Written Opinion, Application No. PCT/US2023/074269, pp. 1-16 (Feb. 9, 2024).
International Search Report and Written Opinion, Application No. PCT/US2023/074277, pp. 1-13 (Feb. 9, 2024).
International Search Report and Written Opinion, Application No. PCT/US2023/074270, pp. 1-21 (Mar. 5, 2024).
International Search Report and Written Opinion, Application No. PCT/US2023/074272, pp. 1-15 (Feb. 9, 2024).
International Search Report and Written Opinion, Application No. PCT/US2023/074273, pp. 1-16 (Mar. 1, 2024).
International Search Report and Written Opinion, Application No. PCT/US2023/074275, pp. 1-16 (Mar. 1, 2024).

\* cited by examiner

Microspheres of Spray-Dried Plasma

20 microns scanning electron microscopy of spray-dried plasma

Figure 1

Spray-Drying Minimally Affects Coagulation Protein Profile

Figure 2

Native Coagulation Pathway Turnover with Spray-Dried Plasma

Fibrin Ultrastructure from Spray-Dried Plasma

— 100 nanometers    Scanning Electro-microgram of Fibrin Clot

Figure 7

Ristocetin Agglutination of Spray-Dried RL Platelets
Visible Microscopy

A- Before Ristocetin

B- After Ristocetin

— 20 microns

— 20 microns

Figure 8

SPRAY-DRIED BLOOD PRODUCTS AND METHODS OF MAKING SAME

CROSS REFERENCE TO RELATED APPLICATIONS

This application is a divisional application of U.S. application Ser. No. 15/872,727 filed Jan. 16, 2018, which is a continuation of U.S. National Phase application Ser. No. 13/262,931 filed Oct. 13, 2011 (now U.S. Pat. No. 9,867,782), which claims the benefit of International Application No. PCT/US2010/030031 having an international filing date of Apr. 6, 2010, which claims the benefit of U.S. Provisional Patent Application No. 61/212,321 filed Apr. 9, 2009, each of which is incorporated herein by reference in its entirety.

BACKGROUND OF THE INVENTION

Field of the Invention

The present invention is directed to methods of preparing dried blood products using spray-drying as an alternative to conventional lyophilization (freeze-drying), and products made by the method. Using the method of the invention, increased recovery rates of dried product are possible. The final product displays at least three-fold concentration over native plasma, as well as increased reconstitution rates when mixed with liquids.

Brief Description of the Related Art

Spray-drying is a technology in which a solution is atomized in a stream of flowing gas for rapid solvent vaporization (e.g., dehydration). The result is the formation on a sub-second timescale of microparticles composed of the residual solute. Spray-drying has been used as a industrial process in the material,[4] food[5] and pharmaceutical[6,7] industries for decades. (e.g., see Bergsoe[8] for an earlier review). More recently, spray-drying has facilitated the preparation of protein therapeutics as microparticles for inhalation,[9] the formulation of advanced carrier-therapeutic microstructures,[10-12] and new classes of micromaterials.[13-15] The role of kinetic, phase transition, mass transfer, heat transfer, and other physical processes in determining ultimate particle size and composition are well-understood (e.g., see Vehring[16] for a recent review), and research in spray-drying is an extremely active area in materials science research. An important finding from this body of research is that in aqueous systems the heat of vaporization reduces the temperature of the particles during the volatilization process. Thus, thermal denaturation of proteins can be minimized for preservation of protein activities.

During World War II, the benefits of whole blood transfusion were appreciated, but logistical difficulties related to collection, transport, outdating and typing mismatch for transfusion reactions limited widespread utilization[17]. Dried plasma was thus developed as a surrogate for whole blood[18]. American, British and Canadian military transfusion services extensively utilized dried plasma[1] during World War II with a very favorable safety profile. The methods for preparing U.S. Army-Navy dried plasma were originally scaled to commercial volumes by Sharp and Dohme, Inc. (and later by a larger industrial consortium) with lyophilization technologies analogous to today's freeze-drying protocols[19]. The dried U.S. Army-Navy plasma was anticoagulated with 0.67% (w/v) sodium citrate, and after 1942 was rehydrated with 0.1% (w/v) citric acid. Rehydration with citric acid was found to result in a final product pH of 7.4-7.6 for a more favorable preservation of thrombin generation[20].

Dried U.S. Army-Navy plasma was placed in widespread civilian use after 1945, and used in the initial phases of the Korean War. However, despite nascent development of ultraviolet irradiation microbial decontamination methods[21], the production of dried plasma was suspended in 1953, the stated reason being hepatitis contamination. However, civilian use of plasma, mostly as fresh frozen plasma, has greatly expanded, with over 13 million units being collected in 2005[22]. In current medical practice plasma is used for a variety of indications, one of the most important being as a component of resuscitation mixtures in trauma with massive blood loss. Plasma contains components, such as the coagulation factors and fibrinogen, which are frequently diminished in hemorrhagic shock-related coagulopathies (e.g., see Hardy et al.[23]).

Several medical findings point towards the utility of a hyper-concentrated plasma product. The desirability of low volume resuscitation, as facilitated by products such as hyper-concentrated plasma, is becoming increasingly accepted since the initial observations of adverse outcomes related to standard resuscitation.[24-26] Incidences of transfusion associated cardiac overload and fluid overload-associated acute respiratory distress syndrome might be avoided with low volume resuscitation.[27,28] Administration of reduced volumes can also be desirable if ongoing hemorrhage is exacerbating dilutional coagulopathies (e.g. see Stern for a review[29]). The development of advanced resuscitation products, such as hemoglobin-based oxygen carriers (HBOCs),[30] facilitate the ability to achieve adequate tissue oxygenation without infusion of large volumes of fluids. However, the introduction of HBOCs is anticipated to create a need for low volume products to supplement hemostatic systems, such as concentrated plasma.

Dried blood products are known in the art, and the predominant technique for achieving the dried product is lyophilization (freeze-drying). For example, U.S. Pat. Nos. 4,287,087 and 4,145,185 to Brinkhous et al. disclose dried blood platelets that have been fixed with a crosslinking reagent such as formaldehyde. U.S. Pat. Nos. 5,656,498, 5,651,966; 5,891,393; 5,902,608; and 5,993,804 disclose additional dried blood products. Such products are useful for therapeutic purposes because they are stable, have long shelf life, and can be used potentially in powder form to arrest bleeding in patients undergoing severe trauma. However, such products must be manufactured under strict sterile conditions in order to avoid contamination.

With current transfusion practices, plasma is frequently provided as a thawed single donor "fresh frozen" product. However, since refrigeration is difficult to provide in forward military applications, underdeveloped countries, and in wilderness medicine situations, this form factor can be logistically problematic. Thus, the elimination of freezing (lyophilization) via a dried plasma product would be a significant advantage. In addition, the dried plasma product is significantly easier to pathogen reduce than is fresh frozen plasma. The present invention is believed to be an answer to that need.

SUMMARY OF THE INVENTION

In one embodiment, the present invention is directed to a method of preparing dehydrated blood products, comprising the steps of: (a) providing a hydrated blood product; (b)

spray-drying the hydrated blood product to produce a dehydrated blood product, as well as dehydrated blood products made by the method.

In another embodiment, the present invention is directed to a method of treating a patient suffering from a blood-related disorder, comprising the steps of: (a) rehydrating a therapeutic amount of the dehydrated blood products to produce a rehydrated therapeutic composition; and (b) administering the rehydrated therapeutic composition to the patient.

In another embodiment, the present invention is directed to a bandage or surgical aid comprising the dehydrated blood products described above.

In yet another embodiment, the present invention is directed to a method of preparing dehydrated fixed blood platelets, comprising the steps of: (a) providing hydrated fixed blood platelets; and (b) spray-drying the hydrated fixed blood platelets to produce a dehydrated fixed blood platelets, as well as dehydrated fixed blood platelets made by the method.

In yet another embodiment, the present invention is directed to a method of treating a patient suffering from a blood-related disorder, comprising the steps of: (a) rehydrating a therapeutic amount of the dehydrated fixed blood platelets to produce a rehydrated therapeutic composition; and (b) administering the rehydrated therapeutic composition to the patient.

In yet another embodiment, the present invention is directed to a bandage or surgical aid comprising the dehydrated fixed blood platelets described above.

In yet another embodiment, the present invention is directed to spray dried fixed blood platelets having spherical-dimpled geometry, wherein when said spray dried fixed blood platelets are rehydrated to form a rehydrated fixed blood platelet composition, the composition has a turbidity ($A_{500}$) value less than that of a comparable rehydrated lyophilized composition of fixed blood platelets.

These and other embodiments will become evident on reading the following detailed description of the invention.

BRIEF DESCRIPTION OF THE DRAWINGS

FIG. 1 is an electron micrograph of microspheres of spray-dried plasma produced according to the present invention;

FIG. 2 is a graph showing coagulation factor levels in various samples;

FIG. 7 is another electron micrograph of rehydrated spray-dried derivatized blood platelets; and FIG. 8 are electron micrographs illustrating ristocetin agglutination of spray-dried rehydrated platelets made according to the method of the invention.

DETAILED DESCRIPTION OF THE INVENTION

Figure 3:
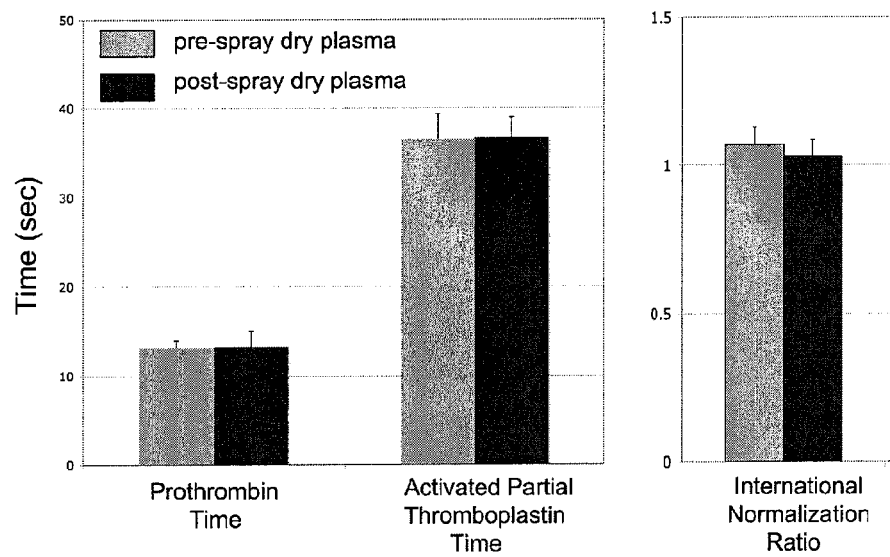
FIG. 3 depicts graphs showing native coagulation pathway turnover with spray dried plasma produced according to the method of the invention.

As indicated above, the present invention is directed to methods of preparing dehydrated blood products, and dehydrated blood products made by the method. Useful hydrated blood products that may be dehydrated by the method of the invention include, but are not limited to, whole blood, blood plasma, blood platelets, red blood cells, blood serum, plasma, and combinations of these. One particularly useful blood product that is suitable for the method of the present invention is blood platelets that have been fixed with a fixative agent, such as formaldehyde or paraformaldehyde. Additionally, the blood products may be modified with additional diagnostic or therapeutic agents, such as imaging agents, concentration factors, performance enhancement drugs, antimicrobial and antiviral reagents, universal donor solutions, and the like, as well as combinations of these. One example of a useful modified product is STASIX (derivatized dried blood platelets) available from Entegrion, Inc. (Research Triangle Park, NC).

The technique of spray-drying is used in the method of the invention as an alternative to conventional drying techniques known in the art, such as lyophilization (freeze drying). Spray drying is a method of transforming material in a fluid state into a dried particulate form by spraying a feed of a material into a warm drying medium. Spray drying involves evaporation of moisture from an atomized feed by mixing the spray and the drying medium in a controlled fashion. The drying medium is typically air, although other gases such as nitrogen may also be used. The drying proceeds until the desired moisture content is reached in the sprayed particles and the product is then separated from the drying medium.

The complete process of spray drying basically consists of a sequence of four processes. The dispersion can be achieved with a pressure nozzle, a two fluid nozzle, a rotary disk atomizer or an ultrasonic nozzle. Selection upon the atomizer type depends upon the nature and amount of feed and the desired characteristics of the dried product. The higher the energy for the dispersion, the smaller are the generated droplets. The manner in which spray contacts the drying air is an important factor in spray dryer design, as this has great bearing on dried product properties by influencing droplet behavior during drying. In one embodiment, the material is sprayed in the same direction as the flow of hot air through the apparatus. The droplets come into contact with the hot drying gas when they are the most moist. In another embodiment, the material is sprayed in the opposite direction of the flow of hot gas. The hot gas flows upwards and the product falls through increasingly hot air into the collection tray. The residual moisture is eliminated, and the product becomes very hot. This method is suitable only for thermally stabile products. In yet another embodiment, the advantages of both spraying methods are combined. The product is sprayed upwards and only remains in the hot zone for a short time to eliminate the residual moisture. Gravity then pulls the product into the cooler zone. This embodiment is particularly advantageous because the product is only in the hot zone for a short time, and is less likely to be affected by heat.

In the spray drying method, air is mostly used as drying medium, but other gases such as nitrogen may also be used. The gas stream is heated electrically or in a burner and after the process exhausted to atmosphere. If the heating medium is recycled and reused, typically an inert gas such as nitrogen, is used instead of air. Use of nitrogen is advantageous when flammable solvents, toxic products or oxygen sensitive products are processed.

During the spray drying process, as soon as droplets of the spray come into contact with the drying gas, evaporation takes place from the saturated vapor film which is quickly established at the droplet surface. Due to the high specific surface area and the existing temperature and moisture gradients, heat and mass transfer results in efficient drying. The evaporation leads to a cooling of the droplet and thus to a small thermal load. Drying chamber design and air flow rate provide a droplet residence time in the chamber, so that the desired droplet moisture removal is completed and product removed from the dryer before product temperatures can rise to the outlet drying air temperature. Hence, there is little likelihood of heat damage to the product.

Two systems are used to separate the product from the drying medium. First, primary separation of the drying product takes place at the base of the drying chamber, and second, total recovery of the dried product in the separation equipment. In one embodiment, a cyclone is used to collect the material. Based on inertial forces, the particles are separated to the cyclone wall as a down-going strain and removed. Other systems such as electrostatic precipitators, textile (bag) filters or wet collectors like scrubbers, may also be used to collect the dried product.

As used in the present invention, spray drying offers advantages over other drying methods such as lyophilization (freeze drying). Use of spray drying produces a product that is more consistent, less clumpy, and better dispersed than freeze drying methods. The highly dispersed particles produced by spray drying also allow for a rapid rehydration rate, which is likely a result of a larger available surface area. By contrast, the clumped nature of a freeze dried product, results in substantially longer rehydration times for the blood products that are dried in the method of the invention. Since many transfusions and other uses of blood products can be highly time-sensitive, this higher rate of rehydration can be a significant advantage in battlefield or emergency treatment situations. As explained in more detail below, spray dried fixed blood platelets of the invention can be rehydrated to form a rehydrated fixed blood platelet composition, and the composition has a turbidity ($A_{500}$) value less than that of a comparable rehydrated lyophilized composition of fixed blood platelets.

The spray-dried products of the method of the invention may be used as topical treatments in treating wounds. In one embodiment, the products may be used directly on a wound to assist clotting, or may be applied to a bandage or surgical aid or covering to assist in wound healing. In an alternative embodiment, the rehydrated forms of the spray-dried products of the method of the invention may be administered via intravenous injection as therapeutic treatments to patients afflicted with blood-related disorders such as thrombocytopenia (including washout thrombocytopenia), hemorrhagic platelet dysfunction, and trauma victims experiencing severe bleeding.

EXAMPLES

General Design and Methods

Spray-dried Plasma Concentration. Human pooled solvent-detergent treated plasma (Kedrion S.p.A., Barga, Italy) and porcine plasma from a pool of ten animals (donated by the Francis Owen Blood Research Laboratory, University of North Carolina at Chapel Hill) can be spray-dried over a range of instrumental run parameters or freeze-dried with a standard lyophilization cycle to obtain different sized dehydrated microparticles. The products are then rehydrated with different volumes of sterile water that contain a low concentration of glycine at pH=2.4 to compensate for the loss of protons during the dehydration process and compared to establish the upper limit for concentration. Details of the experiments follow:

Plasma dehydration. Porcine and human plasma can be spray-dried in a Buchi B-270 research spray-dryer at a flow rate of 415 liters $N_2$ per hour at 140° C., 130° C., 120° C., 110° C., and lower if dehydration can be obtained. Runs are preferably performed three times at each temperature and with each type (i.e., porcine and human) plasma. The final product can be analyzed for moisture content and microparticles imaged with scanning electron microscopy. Portions of pig and human plasma may also be lyophilized at −20° C. for three days from a 4 mm layer to obtain a "lyophilization control" cake. As shown in the accompanying Figures, spray-dried material is observed to be a fine powder, and appear as microspheres under the microscope, while lyophilized material forms a cake.

Plasma rehydration. Spray-dried and lyophilization control lots (each in triplicate) are rehydrated with the appropriate volume of sterile water with glycine for 1×, 2×, 3×, 4× and possibly higher hyper-concentration of the plasma. Rehydration can be with glycine solutions at pH=2.4 for a product with a final rehydrated pH=7.4 as follows: 1×−20 mM glycine, 2−×40 mM glycine, 3×−60 mM glycine, 4×−80 mM glycine, etc.

Physical and chemical analysis. The following analysis may be performed with each triplicate sample of starting plasma (pre-spray dry), each lot spray-dried material and the lyophilized control plasma. Comparisons can be made with the Wilcoxon Signed Rank Test, and directionality will be assessed using the Sign test.

Turbidity and rate of solubilization—Optical measurement of the light absorption at 700 nm can assess turbidity as a function of time after initiation of the rehydration reaction.

Viscosity can be estimated with a falling ball viscometer. Coagulation factor levels (including FII, FV, FVII, FVIII, FIX, FX, FXII, FXII, FXIII, protein S, protein C, von Willebrand factor) are measured with ELISA analysis.

Coagulation pathway turnover—Prothrombin times and activated partial thromboplastin times are measured with concentrated plasmas after dilution of the hyper-concentrated solutions to 1×. Final clots are examined with scanning electron microscopy to assess fiber thickness and density.

A concentrated solution preferably will have the appropriate rheology for standard transfusion practice in which coagulation factor levels and activities are within normal intra- and inter-individual ranges of variation. This solution can be utilized for the "most concentrated" infusions in porcine studies described below.

Safety evaluation of concentrated plasma products in pigs. The goal of these studies is to identify a maximum tolerated dose for hyper-concentrated plasma preparations in injured pigs. Animals are subjected to hepatic injuries for blood loss and induction of compensated hemorrhagic shock. Animals are then be infused with hyper-concentrated plasma porcine preparations until an adverse hemodynamic response is noted. At the termination of the experiment animals is sacrificed and subjected to post-mortem analysis for histological evidence of prothrombotic complications. The endpoint of this analysis will be the definition of the relationship between maximum tolerated dose and degree of plasma concentration.

Induction of Shock in Pigs and Infusion of hyper-concentrated plasma. 40 to 50 kg pigs (obtained from the Division of Laboratory Animal Medicine (UNC) breeding colony) are anesthetized.

Analysis of hemodynamic and vasoactive processes. Several sensors are placed to follow hemodynamic and vasoactive processes: a pulmonary artery thermo dilution catheter is inserted via the external jugular vein into a pulmonary artery; micromanometer-tipped catheters are positioned via the left femoral vessels into the right atrium and thoracic aorta; a .22 gauge catheter is inserted into the left femoral artery and connected to a withdrawal pump. Patterns of blood flow are measured by placing Doppler flow probes on the cephalic and mesenteric arteries; this procedure can be supported by carotid artery cut down and laparotomy.

Induction of shock and infusion of hyper-concentrated plasma. Hemorrhagic shock can be induced by withdrawing 40% of total blood volume over a one-hour period. After withdrawal of blood and verification of hemorrhagic shock (mean arterial blood pressure<40 mm Hg, shift in cephalic, splanchnic blood flow pattern), the animals are infused with multiple doses of 1× spray-dried plasma or hyper-concentrated spray-dried plasma at an intermediate and high level of concentration (to be determined as described above). Each infusion is preferably a volume equivalent to ⅒th of the animal's blood volume, and is preferably performed over a three minute period with a Harvard syringe pump. Hemodynamic and other physiological parameters can be measured, and infusions can be stopped when two successive boluses result in worsening hemodynamic stability. Animals are then be sacrificed for autopsy and histological analysis. The number of animals and the infused products used in this Example are shown in Table 1.

TABLE 1

| Infused Product | Number of Animals |
| --- | --- |
| 1× Plasma | 3 |
| Intermediate Concentration (e.g., 2×) | 3 |
| High Concentration (e.g., 4×) | 3 |
| Total Animals | 9 |

Microvasculopathologies and hemolytic disorders. After sacrifice, selected renal, hepatic, pulmonary, splenic, lung and other tissue are prepared for light microscopic analysis. The histological analysis focuses on identifying signs of macroscopic or disseminated intravascular coagulation or premature induction of selected organ failure.

Data analysis. Comparisons between plasma groups are made with the Wilcoxon Signed Rank Test, and directionality assessed using the Sign test.

Example 1

Spray-Drying of Plasma and Preservation of Coagulation Protein Activities

The following series of experiments demonstrate that plasma can be spray-dried to obtain dehydrated microparticles, and then rehydrated to the original volume for plasma with native coagulation factor levels and coagulation parameters. Solvent-detergent pooled plasma was subjected to standard spray-drying (415 liters $N_2$ per hour at 120° C. in Butchi, Inc. B-270) to obtain the product depicted in FIG. 1. The spherical-dimpled geometry of the resulting microparticles is similar to the shapes obtained when other proteins are spray-dried, indicating that a protein surface shell forms as a result of the initial kinetics of water removal and concentration (e.g., see Vehring[16]). However, this geometry is distinctive over lyophilized plasma which displays a jagged surface texture.

Figure 4:
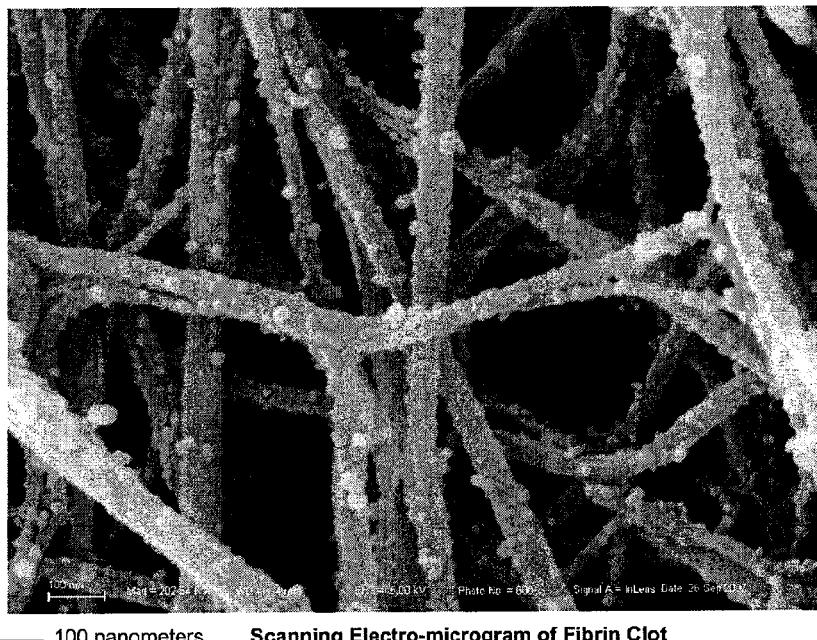
FIG. 4 is an electron micrograph showing fibrin ultrastructure from spray dried plasma produced according to the method of the invention.

Upon rehydration with 20 mM glycine, pH=2.4 to compensate for proton loss during the drying process for the original protein concentration, the coagulation factor levels were found to be essentially the same as in the original plasma before spray drying as shown in FIG. 2. Spray-drying also had an insignificant effect on the kinetics of plasma coagulation (FIG. 3). There was a statistical trend (that was not significant in this analysis) towards enhanced coagulation protein molecular turnover after spray-drying, an effect that might be related to differences in the association states of proteins in plasma samples. The fibrin strands after spray-dried plasma fibrinogen polymerization had normal morphology (FIG. 4).

Figure 5:
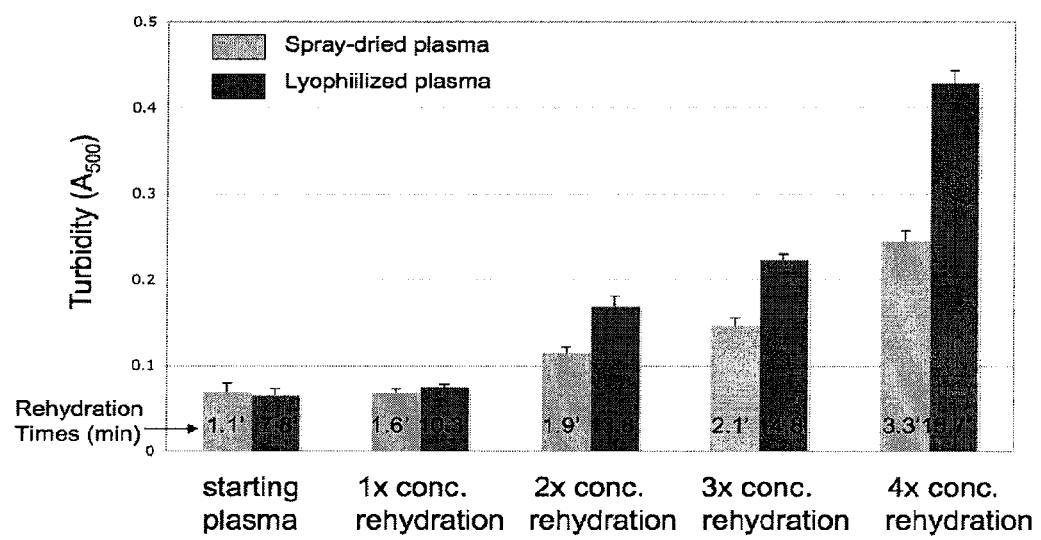
FIG. 5 is a graph depicting the turbidity and rehydration rate of spray-dried vs. lyophilized plasma at several concentrations.

In contrast to the methods of the present invention, freezing and lyophilized plasma results in a product that contains microscopic and macroscopic domains of varying composition due to phase separation. The result is that rehydration at super-physiological concentrations is time consuming and results in a turbid suspension. This point is demonstrated by the data presented in FIG. 5 which shows $A_{500}$ (turbidity) for several concentrations of rehydrated plasma. The solvent-detergent treated plasma product was subjected to spray-drying or lyophilization, then rehydrated for native (1×), 2×, 3× or 4× final concentration. Rehydration times, based on the time for macroscopic dissolution to occur, was dramatically faster with the spray-dried material due to the massive surface area of the microparticle formulation, and results in a significantly less turbid suspension as shown by lower $A_{500}$ values in FIG. 5.

In addition to the plasma described above, other blood products may be dried and rehydrated in accordance with the description above. Virtually any treated or untreated blood product may be used in the method of the invention. Examples of blood products include whole blood, blood plasma, blood platelets, red blood cells, blood serum, as well as combinations of these. The blood products may be used in the method of the invention in their naturally occurring state, or may be modified in any way. Examples of modifications of these blood products include fixation with a fixing agent such as formaldehyde or paraformaldehyde as described in U.S. Pat. Nos. 5,651,966; 5,891,393; 5,902,608; and 5,993,804; addition of imaging agents, concentration factors, performance enhancement drugs, antimicrobial and antiviral reagents and universal donor solutions. One example of a useful modified product is STASIX (derivatized dried blood platelets) available from Entegrion, Inc. (Research Triangle Park, NC). The following is a general protocol for rehydration of spray-dried STASIX particles.

Example 2

Rehydration of Spray Dried Derivatized Blood Platelets

The goal of this example is to rehydrate spray-dried derivatized blood platelets (sold under the tradename STASIX and available from Entegrion, Inc., NC) so that the concentration of all components (platelet particles, buffer salts, bulking agents (e.g., human serum albumin)) are the same as the suspension that went into the spray-drier. This was achieved in three stages.

First, a "reference $A_{280}$ value" for the bulking medium used for the pre-spray-dried suspension is obtained. This is an $A_{280}$ nm value for the pre-spray-dry after the platelets are spun out, reflecting the supernatant protein concentration, which is largely human serum albumin bulking agent. Second, a trial rehydration with the post-spray-dried powder is performed at 10% (w/v), then the optical density at 280 nm ($A_{280}$) of the bulking agent (human serum albumin) is measured. Third, the pre-spray-dried supernatant $A_{280}$ and 10% supernatant $A_{280}$ values are compared (ratioed) to determine how far off the 10% rehydration approximation was. This ratio is then used to calculate the exact weight percentage of dried powder that is needed to match the bulking agent protein concentration of the pre-spray dried suspension.

The platelet count of the post-rehydration particles are then measured two ways. First with a Hiska cell counter and second by measuring the optical turbidity. These values, and related rehydration volumes, form the starting point for all the particle characterization assays.

Procedure

1. Measure the optical density of the pre-spray dry to obtain the reference $A_{280}$ value.
   a) Thaw the liquid pre-spray dry sample and spin out the particles by centrifuging on a desktop microfuge at a setting of five for two minutes. Retain the supernatant.
   b) Dilute the supernatant 1/10 into citrated saline in triplicate and measure $A_{280}$ values with the nanodrop spectrometer.
2. Measure protein optical density of 10% (w/v) suspension
   a) Weigh out several (approximately 4) 20-50 mg particle portions in microfuge tubes. Record the mass. Rehydrate one tube with distilled water for a 10% (w/v) suspension. Save the remaining tubes for future analysis.
   b) Spin out particles as above and retain supernatant.
   c) Dilute each rehydrated sample supernatant 1/10 into citrated saline in triplicate and measure the $A_{280}$ values.
3. Calculate the rehydration weight percentage to match the pre-spray dried value as follows.
   a) Divide the $A_{280}$ values from the diluted pre-spray dry supernatant by the dilution factor (1/10) and average the three values to obtain a theoretical reference $A_{280}$ value or $A_{280,\ ref}$
   b) Divide the $A_{280}$ values form the 10% rehydration supernatant by the dilution factor (1/10) and average the three values to obtain a theoretical undiluted $A_{280}$ value, referred to as $A_{280,\ 10\%}$.
   c) Ratio $A_{280,\ 10\%}$ to the $A_{280,\ ref}$ value according to Equation 1 to obtain the proper rehydration mass (w/v) of post spray-dry powder so that the rehydrated sample will have the same $A_{280}$ value as the reference $A_{280}$ value.

Weight percentage (w/v)*=10% (w/v)×
$A_{280,ref}/A_{250,10\%}$ (Equation 1)

*weight percentage can be in units of mg/ml, e.g., 8.9% (w/v) is equivalent to 89 mg/ml.

Measurement of STASIX Particle Counts
   a) Dilute the 10% rehydration suspension (don't perform the cell spin out) 1/10 with citrated saline in triplicate.
   b) Measure the turbidity at $A_{500}$ of each sample.
   c) Measure the direct cell count with the Hiska hematological analyzer.
   d) Calculate and factor in yield loss.

Figure 6:
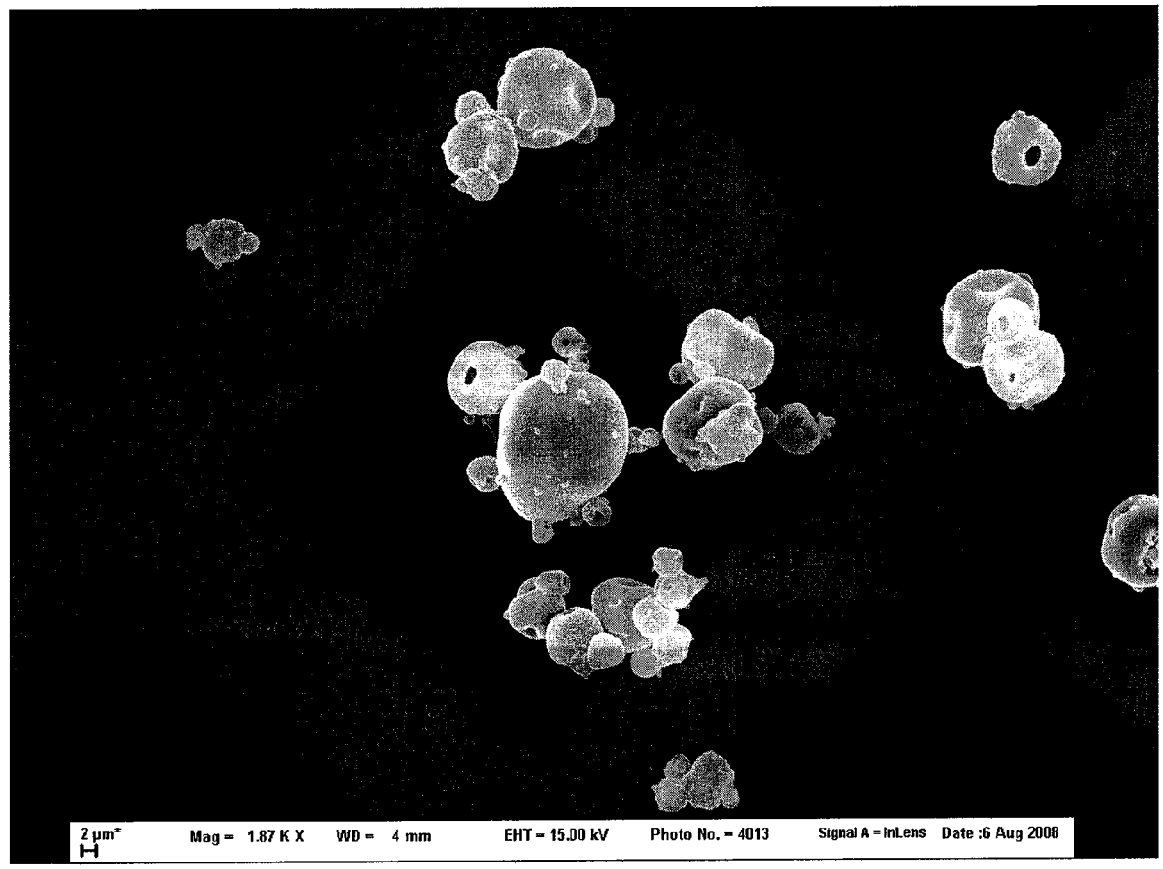
FIG. 6 is an electron micrograph of rehydrated spray-dried derivatized blood platelets.

Electron micrographs of rehydrated spray-dried derivatized blood platelets (rehydrated STASIX) are shown in FIG. 6 and FIG. 7.

Example 3

Single Dose Range-Finding Intravenous Toxicity Study in Cynomolgus Monkeys

A study was designed to assess the toxicity of spray-dried derivatized dried blood platelets (spray-dried Stasix as described above, then rehydrated) when administered via intravenous infusion (over approximately 5 minutes) to monkeys as a single dose. A recovery subgroup of the animals was observed for 7 days.

Five groups of monkeys were used—Group 1—vehicle (buffer) control; Group 2—1× therapeutic STASIX dose; Group 3—5× therapeutic STASIX dose; Group 4—10× therapeutic STASIX dose; and Group 5—human serum albumin (500 mg/kg). Dosages were respectively 0.0, 2.1× $10^9$, $1.05 \times 10^{10}$, $2.1 \times 10^{10}$, and 0.0 platelets/kg in group 1, 2, 3, 4, and 5. A 1× dose is the estimated therapeutic STASIX dose in a human patient, i.e., an additional 30,000 platelet particles per microliter of blood.

No adverse effects either symptomatic or micro-pathologic were seen in any of the monkeys used in this experiment. Since 2 male monkeys and 2 female monkeys all tolerated a 10× therapeutic dose of STASIX infused over the very brief time period of only 5 minutes, the no observable adverse effect level (NOAEL) is at least 10× the therapeutic dose. In a human clinical setting, STASIX doses would be infused at a much slower time rate of 20 minutes.

Necropsy of the 14 study monkeys comprising the 5 dosing groups was conducted at either Day 2 or Day 8 following infusion, and showed no evidence of the development of microthrombi in either the heart or lungs. In summary, in a detailed animal study conducted by a major outside research laboratory under all appropriate animal use and handling regulations, STASIX was shown to display no harmful effects at either a macroscopic or microscopic level at doses up to 10 times the intended human therapeutic dose.

Example 4

Spray-Drying of Aldehyde Stabilized Platelets

The utility of spray-drying as an alternative to lyophilization for the dehydration of aldehyde-stabilized platelets is examined in this example. Human apheresis platelets were stabilized using the procedure of Read et al. described in U.S. Pat. No. 5,651,966, which is herein incorporated by reference in its entirety.

Spray-drying (415 liters $N_2$ per hour at 120° C.) of the final aldehyde-stabilized platelet suspension at 2.0 million platelets/microliter in 5% (w/v) human serum albumin as described above resulted in a fine powder that, upon examination, consisted of spherical particles with 3 to 30 micron diameters similar to those shown in FIGS. 6 and 7.

Seventeen independent dried platelet preparations were prepared with spray-drying and then rehydrated for the original pre-dehydration volumes. The yield (post-rehydration/pre-spray drying) of countable platelets was 96.8%+/−7.0% (standard deviation) for these seventeen runs.

FIG. 8 depicts spray-dried platelets after rehydration, exchange into normal human plasma (as a von Willebrand factor source) and addition of ristocetin to 1 mg/ml (Panel B) or a corresponding volume of control buffer (Panel A). Large aggregates were noted with ristocetin addition, indicating that spray-drying preserved glycoprotein 1B—von Willebrand factor receptor functions.

Cynomolgus monkeys (1 or 2/sex/group) received a single 5-minute intravenous infusion of the spray-dried platelets at doses of $2.1 \times 10^9$, $1.05 \times 10^{10}$, or $2.1 \times 10^{10}$ platelets/kg. Control animals (2/sex) received vehicle (5.375 mM sodium citrate and 2 mM cysteine in physiological saline) and an additional group received 500 mg/kg human serum albumin (HSA). The dose volume was 2 mL/kg/min for all groups. Animals were observed for 1 or 7 days post-dose.

One day after dose administration, 1 animal/sex/group was euthanized and necropsied. One animal per sex from the control and high-dose ($2.1\times10^{10}$ platelets/kg) groups were held for 7 days prior to necropsy. Parameters evaluated during the study were viability, clinical observations, body weights, clinical pathology (pretest, day 2 and day 8), organ weights, macroscopic observations and microscopic pathology.

Administration of all doses of spray-dried platelets (up to $2.1\times10^{10}$ platelets/kg) was well tolerated. Hematology changes were limited to a decrease in the number of platelets and an increase in mean platelet volume in one of the two high-dose ($2.1\times10^{10}$ platelets/kg) animals (the female) on the day following dose administration. There were no observed changes in coagulation or clinical pathology parameters. Increases in spleen weight, relative to control values, were seen in all test article- and HSA-treated animals. Microscopic observations showed slight to moderate increases in the size of germinal centers in the spleen in mid- and high-dose ($1.05\times10^{10}$ or $2.1\times10^{10}$ platelets/kg) females and the HSA-treated female on day 2 and the high-dose female (only group necropsied) on day 8 that correlated with macroscopic observations of tan discoloration and surface abnormalities of the spleen in some animals. Germinal center enlargement in females was considered a possible response to HSA. Similar findings were not seen in the vehicle treated control, which had smaller germinal centers. However, because active germinal centers are a common finding in monkey spleens, and because the sample size was small, this finding may be within normal background range. The persistence of splenic germinal center enlargement after 7 days in one animal suggests lack of recovery, which would be consistent with germinal center reaction to antigenic stimulation, but this finding may also reflect normal background variation.

Example 5

Spray-Drying of Plasma and Testing in Pigs

Plasma separated from fresh porcine blood was either stored as fresh frozen plasma (FFP) or preserved as freeze dried plasma (FDP) or spray-dried plasma (SDP, prepared as detailed in previous examples). For in-vitro testing: SDP was reconstituted in distilled water which was either equal (1×SDP) or one-third (3×SDP) the original volume of FFP. Analysis included measurements of prothrombin time (PT), partial thromboplastin time (PTT), fibrinogen levels, and activity of selected clotting factors. For in-vivo testing swine were subjected to polytrauma (femur fracture, grade V liver injury) and hemorrhagic shock (60% arterial hemorrhage, with the "lethal triad" of acidosis, coagulopathy and hypothermia), and treated with FFP, FDP, or 3×SDP (n=4-5/group). Coagulation profiles (PT, PTT, thromboelastography) were measured at baseline (BL), post-shock (PS), post crystalloid (PC), treatment (MO), and during 4 hours of monitoring (M 1-4).

In-vitro testing revealed that clotting factors were preserved after spray-drying. The coagulation of FFP and 1×SDP were similar, with 3×SDP showing a prolonged PT/PTT. Polytrauma/hemorrhagic shock produced significant coagulopathy, and 3×SDP infusion was as effective as FFP and FDP in reversing it. These results show that plasma can be spray-dried, and reconstituted to one-third its original volume without compromising the coagulation properties in-vivo. This shelf-stable, low-volume, hyperoncotic, hyperosmotic plasma is a logistically attractive option for the treatment of trauma-associated and other coagulopathies.

REFERENCES

1. Kendrick, B. G. D. B. Blood Program in World War II. *U.S. Government Printing Office* Library of Cong. Cat. No. 64-60006, http://amedd.mil/booksdoc/wwii/blood/default.htm (1964).
2. Ketchum, L., Hess, J. R. & Hiippala, S. Indications for early fresh frozen plasma, cryoprecipitate, and platelet transfusion in trauma. *The Journal of trauma* 60, S51-58 (2006).
3. Erber, W. N. & Perry, D. J. Plasma and plasma products in the treatment of massive haemorrhage. *Best Pract Res Clin Haematol* 19, 97-112 (2006).
4. Smith, M. W. Spray-drying synthetic detergents. *Manufacturing chemist and aerosol news* 22, 186-187 (1951).
5. Heldman, D. R., Hall, C. W. & Hedrick, T. I. Air filtration for the spray drying of dairy products. *Journal of dairy science* 51, 466-470 (1968).
6. Raff, A. M., Robinson, M. J. & Svedres, E. V. Spray-drying of tablet granulations. I. A preliminary report. *Journal of pharmaceutical sciences* 50, 76-79 (1961).
7. Riegelman, S., Swintosky, J. V., Hiquchi, T. & Busse, L. W. Studies on pharmaceutical powders and the state of subdivision. IV. The application of spray-drying techniques to pharmaceutical powders. *Journal of the American Pharmaceutical Association* 39, 444-450 (1950).
8. Bergsoe, C. Progress in spray-drying. *Manufacturing chemist and aerosol news* 20, 72-75 (1949).
9. Maltesen, M. J., Bjerregaard, S., Hovgaard, L., Havelund, S. & van de Weert, M. Quality by design—Spray drying of insulin intended for inhalation. *Eur J Pharm Biopharm* 70, 828-838 (2008).
10. Borghetti, G. S., Lula, I. S., Sinisterra, R. D. & Bassani, V. L. Quercetin/beta-Cyclodextrin Solid Complexes Prepared in Aqueous Solution Followed by Spray-drying or by Physical Mixture. *AAPS PharmSciTech* (2009).
11. Mohammed, G. A., Puri, V. & Bansal, A. K. Coprocessing of nevirapine and stavudine by spray drying. *Pharmaceutical development and technology* 13, 299-310 (2008).
12. Ochiuz, L. & Peris, J. E. Preparation and characterisation of alendronate-loaded chitosan microparticles obtained through the spray drying technique. *Medicinal chemistry (Shariqah (United Arab Emirates))* 5, 191-196 (2009).
13. Iskandar, F. et al. Production of morphology-controllable porous hyaluronic acid particles using a spray-drying method. *Acta biomaterialia* (2008).
14. Sen, D. et al. Evaporation Driven Self-Assembly of a Colloidal Dispersion during Spray Drying: Volume Fraction Dependent Morphological Transition. *Langmuir* (2009).
15. Zhang, X. et al. Preparation of a dispersible PEGylate nanostructured lipid carriers (NLC) loaded with 10-hydroxycamptothecin by spray-drying. *Chemical & pharmaceutical bulletin* 56, 1645-1650 (2008).
16. Vehring, R. Pharmaceutical particle engineering via spray drying. *Pharmaceutical research* 25, 999-1022 (2008).
17. Churchhill, C. Surgery in World War II. The physiologic effects of wounds. *U.S. Government Printing Office* (1952).
18. Blalock, A. Report on Committee on Transfusion, National Research Council. (1940).

19. Harper, S. B. The preparation and experimental use of dried blood plasma. *Proceedings of Staff Meetings of the Mayo Clinic* 15, 689-694 (1940).
20. Strumia, D. Minutes, meeting of subcommittee on blood substitutes. *Division of Medical Sciences, National Research Council* (1942).
21. Allen, J., Enerson, D., Barron, E. and Sykes, C. Pooled plasma with little or no risk of homologous serum Jaundice. *J.A.M.A.* 152, 1421-1423 (1954).
22. Whitaker, B. a. S., M. The 2005 Nationwide Blood Collection and Utilization Survey Report. *AABB and US Dept. HHS* http://www.aabb.org/apps/docs/05nb-cursrpt.pdf (2005).
23. Hardy, J. F., De Moerloose, P. & Samama, M. Massive transfusion and coagulopathy: pathophysiology and implications for clinical management. *Can J Anaesth* 51, 293-310 (2004).
24. Baxter, C. R. & Shires, T. Physiological response to crystalloid resuscitation of severe burns. *Annals of the New York Academy of Sciences* 150, 874-894 (1968).
25. Shires, T. Initial care of the injured patient. *The Journal of trauma* 10, 940-948 (1970).
26. Shires, T., Coln, D., Carrico, J. & Lightfoot, S. Fluid Therapy in Hemorrhagic Shock. *Arch Surg* 88, 688-693 (1964).
27. Skeate, R. C. & Eastlund, T. Distinguishing between transfusion related acute lung injury and transfusion associated circulatory overload. *Current opinion in hematology* 14, 682-687 (2007).
28. Triulzi, D. J. Transfusion-related acute lung injury: current concepts for the clinician. *Anesthesia and analgesia* 108, 770-776 (2009).
29. Stern, S.A. Low-volume fluid resuscitation for presumed hemorrhagic shock: helpful or harmful? *Current opinion in critical care* 7, 422-430 (2001).
30. Reynolds, P. S., Barbee, R. W., Skaflen, M. D. & Ward, K. R. Low-volume resuscitation cocktail extends survival after severe hemorrhagic shock. *Shock (Augusta, Ga* 28, 45-52 (2007).
31. Fischer, T. H., Merricks, E., Raymer, R., Nichols, T., Hayes, P., Bode, A., Pearce, L. and Manning, J. The co-infusion of rehydrated lyopholized platelets with HBOC-201 for hemostasis in dilutional thrombocytopenia. *Blood* 98, 2250 (2001).
32. Manning, J. E. et al. Selective aortic arch perfusion using serial infusions of perflubron emulsion. *Acad Emerg Med* 4, 883-890 (1997).
33. Manning, J. E. et al. Selective aortic arch perfusion during cardiac arrest: enhanced resuscitation using oxygenated perflubron emulsion, with and without aortic arch epinephrine. *Ann Emerg Med* 29, 580-587 (1997).
34. Manning, J. E. et al. Selective aortic arch perfusion with hemoglobin-based oxygen carrier-201 for resuscitation from exsanguinating cardiac arrest in swine. *Critical care medicine* 29, 2067-2074 (2001).
35. Toung, T., Reilly, P. M., Fuh, K. C., Ferris, R. & Bulkley, G. B. Mesenteric vasoconstriction in response to hemorrhagic shock. *Shock (Augusta, Ga* 13, 267-273 (2000).
36. Brummel-Ziedins, K., Vossen, C. Y., Rosendaal, F. R., Umezaki, K. & Mann, K. G. The plasma hemostatic proteome: thrombin generation in healthy individuals. *J Thromb Haemost* 3, 1472-1481 (2005).
37. Budowsky, E., Ackerman, S., Purmal, A., Edson, C., Williams, M. Methods and compositions for inactivating viruses. U.S. Pat. No. 6,369,048 (2002).
38. Burnouf, T. et al. Nanofiltration of single plasma donations: feasibility study. *Vox Sang* 84, 111-119 (2003).
39. Burnouf-Radosevich, M., Appourchaux, P., Huart, J. J. & Burnouf, T. Nanofiltration, a new specific virus elimination method applied to high-purity factor IX and factor XI concentrates. *Vox Sang* 67, 132-138 (1994).
40. Horowitz, B. a. C., S. Removal of antibodies from blood-derived compositions while retaining coagulation factors. U.S. Pat. No. 5,541,294 (1996).
41. Bakaltcheva, I., O'Sullivan, A. M., Hmel, P. & Ogbu, H. Freeze-dried whole plasma: evaluating sucrose, trehalose, sorbitol, mannitol and glycine as stabilizers. *Thrombosis research* 120, 105-116 (2007).
42. MacLennan, S. & Williamson, L. M. Risks of fresh frozen plasma and platelets. *The Journal of trauma* 60, S46-50 (2006).
43. Solheim, B. G. Universal pathogen-reduced plasma in elective open-heart surgery and liver resection. *Clin Med Res* 4, 209-217 (2006).
44. Noddeland, H. et al. Universal solvent/detergent-treated fresh frozen plasma (Uniplas—rationale and clinical properties. *Thrombosis research* 107 Suppl 1, S33-37 (2002).
45. Medwatch, F. Imporrtant safety information regarding Plas+SD. http://www.fda.gov/medwatch/safety/2002/plassd_deardoc.pdf (2002).
46. Monroe, D. M., Hoffman, M., Allen, G. A. & Roberts, H. R. The factor VII-platelet interplay: effectiveness of recombinant factor VIIa in the treatment of bleeding in severe thrombocytopathia. *Seminars in thrombosis and hemostasis* 26, 373-377 (2000).
47. Monroe, D. M., Hoffman, M. & Roberts, H. R. Platelets and thrombin generation. *Arterioscler Thromb Vasc Biol* 22, 1381-1389 (2002).
48. Deveras, R. A. & Kessler, C. M. Reversal of warfarin-induced excessive anticoagulation with recombinant human factor VIIa concentrate. *Annals of internal medicine* 137, 884-888 (2002).
49. Freeman, W. D. et al. Recombinant factor VIIa for rapid reversal of warfarin anticoagulation in acute intracranial hemorrhage. *Mayo Clin Proc* 79, 1495-1500 (2004).
50. Sorensen, B., Johansen, P., Nielsen, G. L., Sorensen, J. C. & Ingerslev, J. Reversal of the International Normalized Ratio with recombinant activated factor VII in central nervous system bleeding during warfarin thromboprophylaxis: clinical and biochemical aspects. *Blood Coagul Fibrinolysis* 14, 469-477 (2003).
51. Talkad, A., Mathews, M., Honings, D., Jahnel, J. & Wang, D. Reversal of warfarin-induced anticoagulation with factor VIIa prior to rt-PA in acute stroke. *Neurology* 64, 1480-1481 (2005).

What is claimed is:

1. A method of preparing dehydrated plasma, comprising the steps of:
   a) providing hydrated plasma; and
   b) spray drying said hydrated plasma at a temperature of at least about 110° C. to produce dehydrated plasma wherein one or more coagulation factors are retained after drying.

2. The method of claim 1, wherein said hydrated plasma is physically or chemically modified.

3. The method of claim 2, wherein said modification is chemical fixation.

4. The method of claim 2, wherein said modification comprises additional diagnostic or therapeutic reagents.

5. The method of claim 4, wherein said diagnostic or therapeutic reagents are selected from the group consisting of imaging agents, concentration factors, performance enhancement drugs, antimicrobial and antiviral reagents, universal donor solutions, and combinations thereof.

6. The method of claim 1, wherein the one or more coagulation factor include FII, FV, FVII, FVIII, FIX, FX, FXI, FXII, FXIII, protein S, protein C, von Willebrand factor, or a combination thereof.

7. The method of claim 1, wherein the step b) includes spray drying said hydrated plasma at a temperature between about 110° C. and about 140° C.

8. A method of preparing spray dried plasma, comprising the steps of:
   a) providing hydrated plasma; and
   b) spray drying said hydrated plasma by a spray dryer at a temperature of at least about 110° C., wherein when rehydrated, the spray dried plasma has one or more coagulation factor levels of concentration and activity that are essentially the same as said hydrated plasma.

9. The method of claim 8, wherein the one or more coagulation factor include FII, FV, FVII, FVIII, FIX, FX, FXI, FXII, FXIII, proteinS, protein C, von Willebrand factor, or a combination thereof.

10. A method of preparing dehydrated plasma, comprising the steps of:
    a) providing hydrated plasma; and
    b) spray drying said hydrated plasma at a temperature of at least about 110° C. to produce dehydrated plasma; wherein, when rehydrated, the dehydrated plasma has one or more coagulation factor levels that induce clot formation.

11. The method of claim 10, wherein the one or more coagulation factor levels that induce clot formation include FII, FV, FVII, FVIII, FIX, FX, FXI, FXII, FXIII, protein S, protein C, von Willebrand factor, or a combination thereof.

12. The method of claim 10, wherein the step b) includes spray drying said hydrated plasma at a temperature between about 110° C. and about 140° C.

* * * * *